US010092413B2

(12) United States Patent
Gray et al.

(10) Patent No.: US 10,092,413 B2
(45) Date of Patent: Oct. 9, 2018

(54) IMPLANTABLE SYSTEMS, DEVICES AND RELATED METHODS

(71) Applicant: GLOBUS MEDICAL, INC., Audubon, PA (US)

(72) Inventors: Jason Gray, East Greenville, PA (US); Andrew Iott, Newtown Square, PA (US); Noah Hansell, King of Prussia, PA (US); Peter Goldsmith, Wayne, PA (US); Jennifer Klimek, King of Prussia, PA (US)

(73) Assignee: Globus Medical Inc, Audubon, PA (US)

( * ) Notice: Subject to any disclaimer, the term of this patent is extended or adjusted under 35 U.S.C. 154(b) by 0 days.

(21) Appl. No.: 14/933,540

(22) Filed: Jan. 14, 2016

(65) Prior Publication Data

US 2017/0056204 A1 Mar. 2, 2017

Related U.S. Application Data

(63) Continuation-in-part of application No. 14/842,881, filed on Sep. 2, 2015.

(51) Int. Cl.

*A61F 2/44* (2006.01)
*A61B 17/86* (2006.01)

(Continued)

(52) U.S. Cl.

CPC ........ *A61F 2/4465* (2013.01); *A61B 17/8042* (2013.01); *A61B 17/86* (2013.01); *A61F 2/44* (2013.01); *A61F 2/447* (2013.01); *A61B 17/064* (2013.01); *A61B 17/8033* (2013.01); *A61F 2/4611* (2013.01); *A61F 2002/2839* (2013.01); *A61F 2002/302* (2013.01); *A61F 2002/30004* (2013.01); *A61F 2002/305* (2013.01); *A61F 2002/30029* (2013.01); *A61F 2002/3093* (2013.01); *A61F 2002/30112* (2013.01);

(Continued)

(58) Field of Classification Search

CPC ........... A61F 2/4455–2/447; A61F 2002/4475; A61F 2002/448–2002/4485

See application file for complete search history.

(56) References Cited

U.S. PATENT DOCUMENTS 5,397,364 A 3/1995 Kozak et al.
5,458,641 A 10/1995 Jiminez (Continued)

FOREIGN PATENT DOCUMENTS

FR 2727003 A1 5/1996
WO 1997023175 A1 7/1997

(Continued)

OTHER PUBLICATIONS

U.S. Appl. No. 60/777,663, filed Feb. 27, 2006, Messerli.

(Continued)

*Primary Examiner* — Jacqueline Johanas

(57) ABSTRACT

The present application is generally directed to implantable systems, devices and related methods pertaining to spinal surgery. In particular, the present application discloses a frame and spacer system for inserting into a disc space. The frame and spacer system is of low profile. The frame can receive different fixation devices, including threaded and non-threaded fixation devices.

20 Claims, 21 Drawing Sheets

680
650

(51) Int. Cl.
*A61F 2/46* (2006.01)
*A61F 2/30* (2006.01)
*A61B 17/064* (2006.01)
*A61B 17/80* (2006.01)
*A61F 2/28* (2006.01)

(52) U.S. Cl.
CPC ............... *A61F 2002/30131* (2013.01); *A61F 2002/30436* (2013.01); *A61F 2002/30787* (2013.01); *A61F 2002/30828* (2013.01); *A61F 2002/30841* (2013.01); *A61F 2002/30904* (2013.01); *A61F 2002/4475* (2013.01); *A61F 2310/00359* (2013.01)

(56) References Cited

U.S. PATENT DOCUMENTS 5,549,612 A 8/1996 Yapp et al.
5,861,041 A 1/1999 Tienboon
5,888,223 A 3/1999 Bray, Jr.
6,066,175 A 5/2000 Henderson et al.
6,156,037 A 12/2000 LeHuec et al.
6,200,347 B1 3/2001 Anderson et al.
6,206,922 B1 3/2001 Zdeblick et al.
6,231,610 B1 5/2001 Geisler
6,258,089 B1 7/2001 Campbell et al.
6,383,186 B1 5/2002 Michelson
6,432,106 B1 8/2002 Fraser
6,468,311 B2* 10/2002 Boyd ........................ A61F 2/28 623/17.11
6,482,233 B1 11/2002 Aebi
6,540,785 B1 4/2003 Gill et al.
6,558,423 B1 5/2003 Michelson
6,558,424 B2 5/2003 Thalgott
6,666,889 B1 12/2003 Commarmond
6,740,118 B2 5/2004 Eisermann et al.
6,827,740 B1 12/2004 Michelson
6,899,735 B2 5/2005 Coates et al.
6,972,019 B2 12/2005 Michelson
7,001,432 B2 2/2006 Keller et al.
7,025,787 B2 4/2006 Bryan et al.
7,137,997 B2 11/2006 Paul
7,147,665 B1 12/2006 Bryan et al.
7,153,325 B2 12/2006 Kim et al.
7,172,627 B2 2/2007 Fiere et al.
7,232,464 B2 6/2007 Mathieu et al.
7,276,082 B2 10/2007 Zdeblick et al.
7,309,357 B2 12/2007 Kim
7,320,708 B1 1/2008 Bernstein
7,618,456 B2 11/2009 Mathieu et al.
7,771,475 B2 8/2010 Michelson
7,846,207 B2 12/2010 Lechmann et al.
7,862,616 B2 1/2011 Lechmann et al.
7,875,076 B2 1/2011 Mathieu et al.
8,100,976 B2 1/2012 Bray et al.
8,343,222 B2 1/2013 Cope
8,753,400 B2* 6/2014 Ciupik ................. A61F 2/4465 623/17.11
9,398,960 B2* 7/2016 Rosen ..................... A61F 2/442
9,492,286 B2* 11/2016 Biedermann ......... A61F 2/4465
9,539,109 B2* 1/2017 Spangler ............... A61F 2/4455
2002/0010511 A1 1/2002 Michelson
2002/0016595 A1 2/2002 Michelson
2003/0045939 A1 3/2003 Casutt
2003/0105528 A1 6/2003 Shimp et al.
2003/0125739 A1 7/2003 Bagga et al.
2003/0167091 A1 9/2003 Scharf
2004/0078078 A1 4/2004 Shepard
2004/0143270 A1 7/2004 Zucherman et al.
2004/0143332 A1 7/2004 Krueger et al.
2004/0176853 A1 9/2004 Sennett et al.
2005/0055098 A1 3/2005 Zdeblick et al.
2005/0065607 A1 3/2005 Gross
2005/0149192 A1 7/2005 Zuchermann et al.
2005/0149193 A1 7/2005 Zuchermann et al.
2005/0159819 A1 7/2005 McCormack et al.
2005/0171607 A1 8/2005 Michelson
2005/0177236 A1 8/2005 Mathieu et al.
2005/0187625 A1 8/2005 Wolek et al.
2005/0240267 A1 10/2005 Randall et al.
2005/0240271 A1 10/2005 Zubok et al.
2005/0256574 A1 11/2005 Paul et al.
2006/0085071 A1 4/2006 Lechmann et al.
2006/0129240 A1 6/2006 Lessar et al.
2006/0217809 A1 9/2006 Albert et al.
2007/0088441 A1 4/2007 Duggal et al.
2007/0123987 A1 5/2007 Bernstein
2007/0135923 A1 6/2007 Peterman et al.
2007/0162130 A1 7/2007 Rashbaum et al.
2007/0168032 A1 7/2007 Muhanna et al.
2007/0225806 A1 9/2007 Squires et al.
2007/0225812 A1 9/2007 Gill
2007/0233253 A1 10/2007 Bray et al.
2007/0250167 A1 10/2007 Bray et al.
2007/0270961 A1 11/2007 Ferguson
2007/0293948 A1 12/2007 Bagga et al.
2008/0051890 A1 2/2008 Waugh et al.
2008/0051907 A1 2/2008 Marik
2008/0133013 A1 6/2008 Duggal et al.
2008/0306596 A1* 12/2008 Jones .................... A61F 2/4455 623/17.16
2009/0076608 A1 3/2009 Gordon et al.
2009/0099661 A1* 4/2009 Bhattacharya ........ A61F 2/4455 623/17.16
2009/0210062 A1 8/2009 Thalgott et al.
2010/0204737 A1* 8/2010 Bae ...................... A61B 17/846 606/279
2011/0218628 A1* 9/2011 Ciupik ...................... A61F 2/44 623/17.11
2011/0218631 A1* 9/2011 Woodburn, Sr. .......... A61F 2/44 623/17.16
2012/0179259 A1 7/2012 McDonough et al.
2013/0023937 A1* 1/2013 Biedermann ......... A61F 2/4465 606/279
2013/0053962 A1 2/2013 Moskowitz et al.
2013/0073047 A1* 3/2013 Laskowitz ............ A61F 2/4455 623/17.16
2013/0197648 A1* 8/2013 Boehm ..................... A61F 2/44 623/17.16
2014/0067072 A1* 3/2014 Woodburn, Sr. .......... A61F 2/44 623/17.16
2014/0088711 A1 3/2014 Chin et al.
2014/0180422 A1 6/2014 Klimek et al.
2014/0228957 A1 8/2014 Niemiec et al.
2014/0277489 A1* 9/2014 Davenport ............ A61F 2/4455 623/17.16
2016/0242923 A1* 8/2016 Davenport .............. A61F 2/442
2016/0338847 A1* 11/2016 Hewko ................. A61F 2/4425
2016/0367377 A1* 12/2016 Faulhaber ............... A61F 2/447
2017/0000628 A1* 1/2017 McLean .................. A61F 2/447
2017/0056203 A1* 3/2017 Gray ..................... A61F 2/4465
2017/0056204 A1* 3/2017 Gray ......................... A61F 2/44
2017/0095347 A1* 4/2017 McLean .................. A61F 2/447
2017/0143503 A1* 5/2017 Klimek ................... A61F 2/442

FOREIGN PATENT DOCUMENTS

WO 1999063914 A1 12/1999
WO 2005007040 A1 1/2005
WO 2007098288 A2 8/2007
WO 2008014258 A2 1/2008
WO 2015009793 A1 1/2015

OTHER PUBLICATIONS

U.S. Appl. No. 60/777,732, filed Feb. 27, 2006, Messerli et al.
U.S. Appl. No. 60/838,229, filed Aug. 16, 2006, Hunziker et al.
Guidance Document: Intervertebral Body Fusion Device, 115. Dept. of Health and Human Services, Food and Drug Administration. (Jun. 12, 2007).

(56) References Cited

OTHER PUBLICATIONS

M. Spruit et al.,The in vitro stabilizing effect of polyether-etherketone cages versus a titanium cage of similar design for anterior lumbar interbody fusion, 14(8) Eur. Spine J. 752, 752-758 (2005).

P. Schleicher et al., Biomechanical comparison of two different concepts for stand alone anterior lumbar interbody fusion, 17(12) Eur. Spine J. 1757, 1757-1765 (2008).

P.W. Pavlov et al., Anterior lumbar interbody fusion with threaded fusion cages and autologous bone grafts, 9 Eur. Spine J. 224, 224-229 (2000).

Synthes' SynFix Technique Guide device ("SynFix Technique Guide").

* cited by examiner 50
80
84
61
82
58
62

50
80
61
84
89
82
58
62

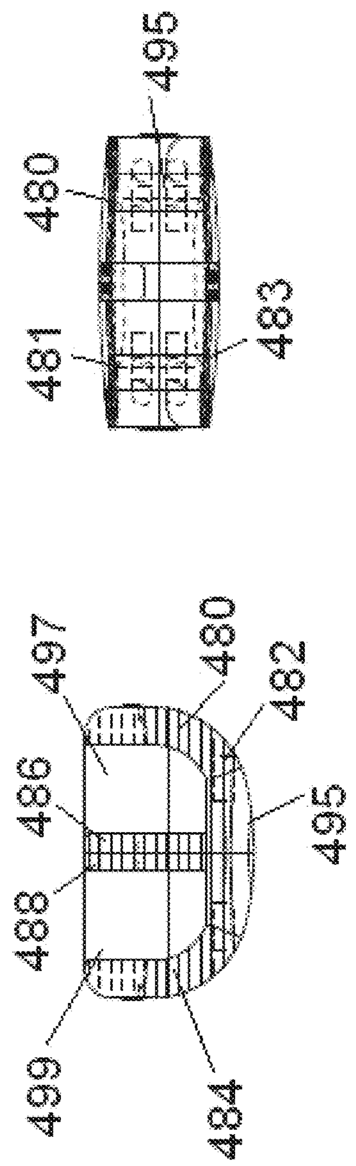
FIG. 25
FIG. 24
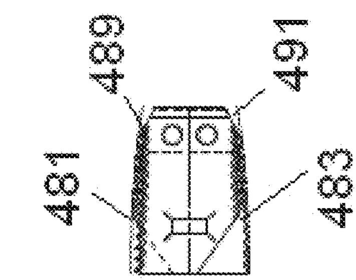
FIG. 26

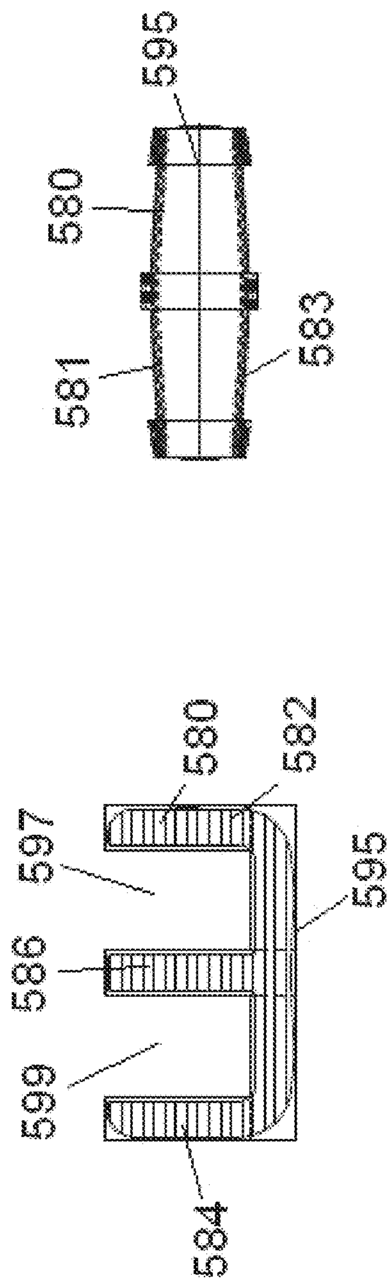
FIG. 28
FIG. 27
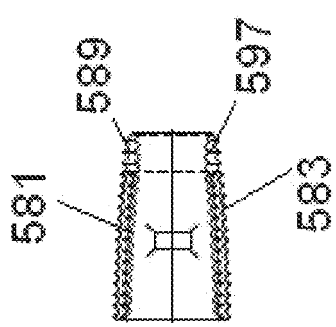
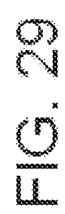
FIG. 29

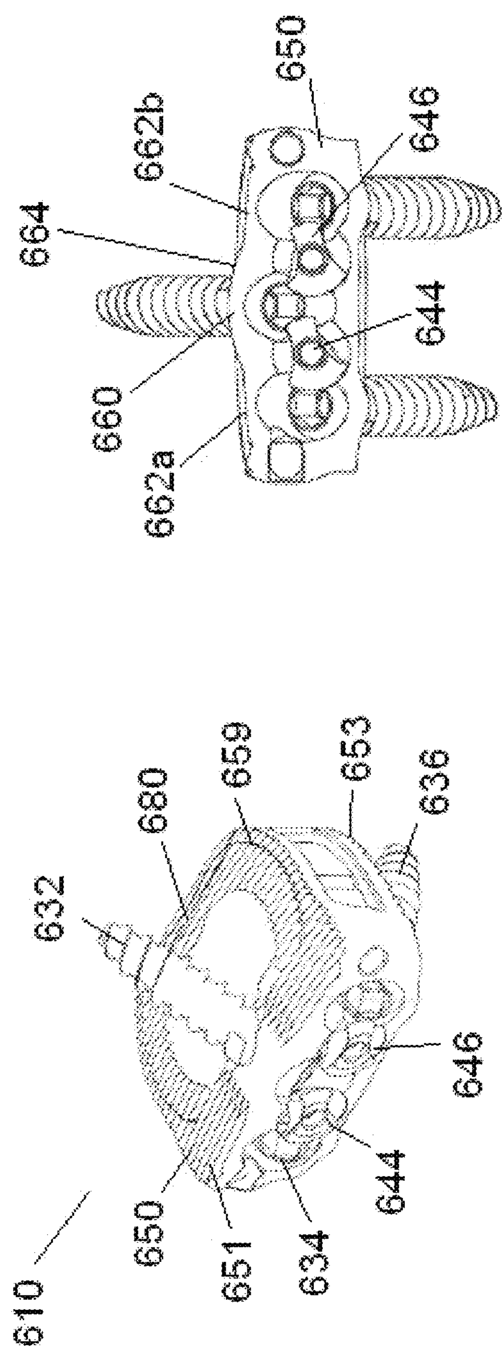
FIG. 31
FIG. 30
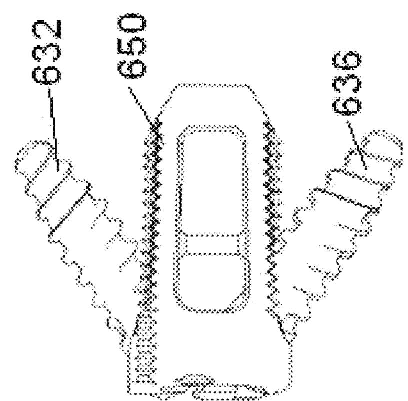
FIG. 32

NEW DRAWING

IMPLANTABLE SYSTEMS, DEVICES AND RELATED METHODS

CROSS-REFERENCE TO RELATED APPLICATIONS

The present application is a continuation-in-part application of U.S. patent application Ser. No. 14/842,881, filed Sep. 2, 2015, which is hereby incorporated by reference in its entirety.

FIELD OF THE INVENTION

The present application is generally directed to implantable systems, devices and related methods pertaining to the spine.

BACKGROUND

Spinal fusion procedures are performed on patients to treat back pain caused by degenerated discs. During spinal fusion procedures, a surgeon restores a disc space back to its original height before inserting an interbody fusion device. Graft material can be deposited within the interbody fusion device to promote fusion and bone growth. There is thus a need for improved systems and devices for promoting fusion of the spine.

SUMMARY OF THE INVENTION

The present application is generally directed in some embodiments to a surgical system comprising a frame, wherein the frame comprises a first side, a second side, a third side, and a fourth side that form a continuous perimeter around a frame opening; a spacer received in the frame opening, wherein the spacer comprises a first arm and a second arm that extend around a spacer opening; and one or more fixation members insertable in the frame, wherein the one or more fixation members includes at least a first fixation member that is angled in an upward direction and a second fixation member that is angled in a downward direction.

In other embodiments, a surgical system comprises a frame, wherein the frame comprises a leading end, a trailing end, a first sidewall, and a second sidewall that form a continuous perimeter around a frame opening; a spacer received in the frame opening, wherein the spacer comprises a first arm and a second arm that extend around a spacer opening; and one or more fixation members insertable in the trailing end of the frame, wherein the one or more fixation members includes at least a first fixation member that is angled in an upward direction and a second fixation member that is angled in a downward direction.

BRIEF DESCRIPTION OF THE DRAWINGS

FIG. 24 is a top view of a spacer including a convex side and a pair of graft chambers in accordance with some embodiments.

FIG. 25 is an anterior view of the spacer of FIG. 24.

FIG. 26 is a side view of the spacer of FIG. 24.

FIG. 27 is a top view of a spacer including a substantially flat side and a pair of graft chambers in accordance with some embodiments.

FIG. 28 is an anterior view of the spacer of FIG. 27.

FIG. 29 is a side view of the spacer of FIG. 27.

FIG. 30 is a top perspective view of an alternative frame and spacer system in accordance with some embodiments.

FIG. 31 is a front view of the alternative frame and spacer system of FIG. 30.

FIG. 32 is a side view of the alternative frame and spacer system of FIG. 30.

DETAILED DESCRIPTION OF THE ILLUSTRATED EMBODIMENTS

The present application is generally directed to implantable systems, devices and related methods pertaining to the spine. In particular, the present application is generally directed to systems and devices for inserting into a disc space of a spine to promote fusion between vertebrae. The systems and devices can be inserted into the spine via any approach, such as posteriorly, transforaminally, laterally or anteriorly. In some embodiments, the systems and devices described herein can be used at least in part as a vertebral body replacement, such that the systems and devices occupy one or more vertebral bodies in addition or instead of one of more disc members.

In some embodiments, a frame and spacer system is provided that can be inserted into a disc space as part of a fusion procedure. Advantageously, the frame is independent from the spacer such that a surgeon can choose the type of spacer (e.g., either PEEK or allograft) to insert within the frame. In addition, if desired, the frame can advantageously be inserted on its own as a standalone device without the spacer in between vertebrae. The frame can be dimensioned to fit between two vertebrae, and can be sturdy enough to support a load from the vertebrae.

Figure 1:
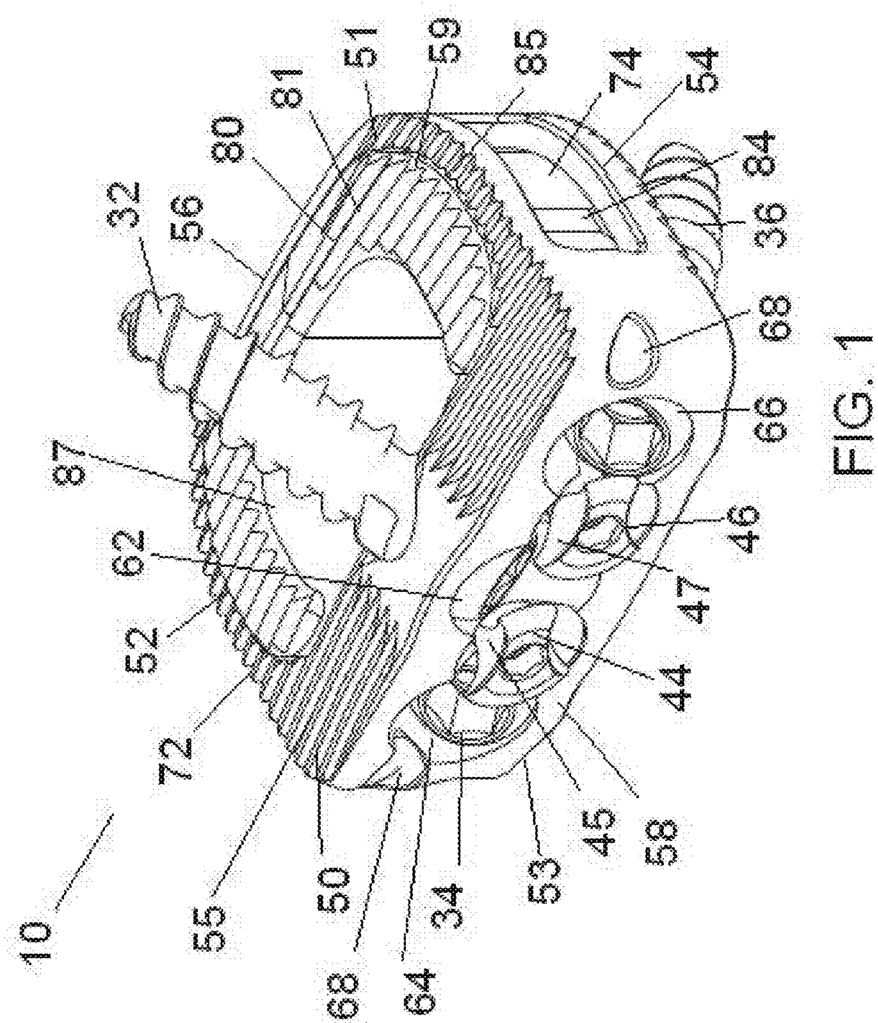
FIG. 1 shows a top perspective view of a frame and spacer system in accordance with some embodiments.

FIG. 1 shows a top perspective view of a frame and spacer system in accordance with some embodiments. The frame and spacer system 10 comprises a frame 50 having fixation members 32, 34, 36 and a spacer 80 received therein. The frame and spacer system 10 is configured to be placed in a disc space and receive graft material therein, thereby promoting spinal fusion and bone growth. In some embodiments, the frame and spacer system 10 is sized and configured such that the entire system is of low profile. Advantageously, as the system 10 is of low profile, the frame 50 and the spacer 80 can be completely received within a disc space such that no portion of it protrudes outside of a disc space. In some embodiments, the system 10 can be sized to replace one or more vertebral bodies, or parts thereof, in addition to one or more disc members.

As shown in FIG. 1, in some embodiments, the frame 50 and the spacer 80 can be of substantially the same height. Advantageously, this allows both the frame 50 and the spacer 80 to share vertebral load. In some embodiments, the upper and lower surfaces of the frame 50 can share the overall contour of the upper and lower surfaces of the spacer 80 and vice versa. For example, in embodiments in which the spacer 80 has a convex upper surface and a convex lower surface, the frame 50 can similarly have a convex upper surface and a convex lower surface. Likewise, in embodiments in which the spacer 80 has a planar upper surface and a planar lower surface, the frame 50 can similarly have a planar upper surface and a planar lower surface. In other embodiments, the spacer 80 can have a height that slightly larger than the frame 50, while still maintaining an overall low profile system. In other embodiments, the frame 50 can have a height slightly larger than the spacer 80, while still maintaining an overall low profile system.

FIG. 1 shows one type of cage or frame 50 in accordance with some embodiments. The frame 50 comprises a first side 52, a second side 54, a third side 56 and a fourth side 58. The first side 52, second side 54, third side 56 and fourth side 58 form a structure having a continuous perimeter. Advantageously, by providing a continuous perimeter that extends around the outside of the spacer 80, the frame 50 is capable of bearing load. As the frame 50 can bear load, the frame 50 can be used on its own as a fusion device within an intervertebral disc space. As shown in FIG. 1, the first side 52, second side 54, third side 56 and fourth side 58 surround an opening 59. A spacer 80 (such as a PEEK or allograft spacer) can optionally be placed in the opening 59 of the frame 50 prior to inserting the frame 50 into a disc space.

With respect to the frame 50, the first side 52 opposes the second side 54. In some embodiments, the first side 52 can comprise a first sidewall and the second side 54 can comprise a second sidewall. The first side 52 comprises a first window 72 and the second side 54 comprises a second window 74. In some embodiments, the first window 72 is configured to receive a first bump out or protruding portion located on the spacer 80 and the second window 74 is configured to receive a second bump out or protruding portion 84 located on the spacer 80. By receiving the protruding portions 84 of the spacer 80 in the windows 72, 74, this advantageously provides regions of secure engagement between the frame 50 and the spacer 80. In some embodiments, to secure the frame 50 to the spacer 80, the spacer 80 can be downwardly forced into the frame 80 (e.g., via hand or a press assembly) until the protruding portions 84 of the spacer 80 are received in the windows 72, 74. At this point the frame 50 is secured to the spacer 80 such that the two members can be delivered securely to a disc space in preparation for bone fusion.

With respect to the frame 50, the third side 56 opposes the fourth side 58. In some embodiments, the third side 56 can comprise a posterior or leading edge, while the fourth side 58 can comprise an anterior or trailing edge. In some embodiments, the third side 56 can comprise a third window 76. In some embodiments, the third window 76 can be configured to receive a bump out or protruding portion on a posterior surface of the spacer 80. In other embodiments, the third window 76 can simply be used to promote fusion by allowing bone growth through it during a spinal fusion procedure.

In some embodiments, the fourth side 58 of the frame 50 can receive fixation members therein to secure the frame 50 to adjacent vertebral bodies. In some embodiments, the frame 50 comprises a first opening 62 for receiving a first fixation member 32, a second opening 64 for receiving a second fixation member 34, and a third opening 66 for receiving a third fixation member 36. The first fixation member 32 is angled in an upward direction to engage an upper vertebra, while the second and third fixation members 34, 36 are angled in a downward direction to engage a downward vertebra. In some embodiments, the frame 50 is of such a low profile that no portion of the fixation members 32, 34, 36 protrudes beyond the disc space. For example, in some embodiments, the fixation members 32, 34, 36 would not enter into the vertebrae through their anterior faces. In other embodiments, only a rear portion of the fixation members 32, 34, 36 (e.g., their heads) protrudes beyond the disc space. And in yet other embodiments, only a small portion of their overall bodies (e.g., including the shaft) protrudes beyond the disc space. In these embodiments, it is possible that a minimal portion of the fixation members 32, 34, 36 can contact the anterior faces of the vertebrae. In some embodiments, the frame 50 is of such a low profile that each of the openings 62, 64, 66 has a majority of or all of their central longitudinal axes positioned between the height of the spacer 80, as defined from an upper surface of the spacer 80 to a lower surface of the spacer 80.

To prevent inadvertent backout of the fixation members 32, 34, 36, the frame 50 further includes a first blocking member 44 and a second blocking member 46. The first blocking member 44 includes one or more cut-out regions 45 that allow first and second fixation members 32, 34 to be received in the first and second openings 62, 64. Once the first and second fixation members 32, 34 are received therein, the first blocking member 44 can be rotated such that a portion of the first blocking member 44 overlies the heads of the each of the first and second fixation members 32, 34, thereby reducing the likelihood of backout of the fixation members. Likewise, the second blocking member 46 includes one or more cut-out regions 47 that allow second and third fixation members 34, 36 to be received in the second and third openings 64, 66. Once the second and third fixation members 34, 36 are received therein, the second blocking member 46 can be rotated such that a portion of the second blocking member 46 overlies the heads of the each of the first and second fixation members 32, 34, thereby reducing the likelihood of backout of the fixation members. In some embodiments, the first and second blocking members 44, 46 do not overlie the heads of the fixation members, but rather about the sides of the heads of the fixation members. Each of the first and second blocking members 44, 46 can be considered "multi-blocking" members, as they block two or more fixation members from backing out. In other embodiments, each of the openings 62, 64, 66 includes its own individual blocking member to reduce the risk of backout of the fixation member.

As shown in FIG. 1, the fixation members 32, 34, 36 comprise threaded screws or fasteners. The screws can include a head portion and a threaded shaft. In some embodiments, the threaded shaft can be tapered to assist in insertion into vertebrae. In other embodiments, different fixation members 32, 34, 36 can be provided. For example, as shown in FIGS. 10-14, non-threaded blades or shims can be inserted into the vertebrae. Advantageously, these alternative fixation members can be inserted into frame via the same openings 62, 64, 66, thereby allowing a user to choose the type of fixation member to use. In some embodiments, the same fixation members (e.g., threaded screws or non-threaded blades) are insertable through the frame 50. In other embodiments, a combination of different types of fixation members (e.g., one threaded screw and two non-threaded blades) are insertable through the frame 50.

The fourth side of the frame 50 can also include first and second tool engagement holes 68. As shown in FIG. 1, one hole 68 is positioned on a first side of the frame 50, while a second hole 68 is positioned on a second side of the frame 50. Each of these holes 68 can be engaged by an insertion tool to facilitate easy delivery of the system 10 into a disc space.

The frame 50 of the system 10 also includes an upper surface 51 and a lower surface 53. The upper surface 51 is configured to engage an upper vertebra, while the lower surface 53 is configured to engage a lower vertebra. In some embodiments, the upper surface 51 and the lower surface 53 can include teeth, protrusions, ribbing or ridges 55 that assist in engagement with an adjacent vertebra.

In some embodiments, the frame 50 can be formed of a metal or metal alloy. In some embodiments, the frame 50 can be formed of titanium, titanium alloy, steel, steel alloy or any other biocompatible material. In some embodiments, the frame 50 is of a different material from the spacer 80 that resides within it. For example, the frame 50 can be formed of titanium, while the spacer 80 can be formed of PEEK or allograft.

FIG. 1 shows one type of spacer 80 in accordance with some embodiments. The spacer 80 is designed to reside in the opening 59 formed in the frame 50. Advantageously, a surgeon can choose the type of spacer 80 (e.g., either PEEK or allograft) to insert into the frame 50, even immediately before a surgical procedure. In some embodiments, a surgeon may desire to promote greater bone growth, thereby choosing an allograft spacer 80. In other embodiments, a surgeon may desire to promote greater structural strength, thereby choosing a PEEK spacer 80.

As shown in FIG. 1, the spacer 80 comprises a C-shaped spacer having an upper surface 81 and an opposing lower surface. The upper and lower surfaces are configured to include teeth, protrusions, ribbing, or ridges 85 that engage adjacent vertebral bodies. The spacer 80 can include an opening 87 formed therethrough in which graft material can be deposited therein. The graft material can be deposited to promote fusion and bone growth. In some embodiments, a plug (e.g., a cancellous plug) can be deposited in the opening 87. In some embodiments, demineralized bone can be deposited in the opening 87 to further promote fusion and bone growth.

Figure 3:
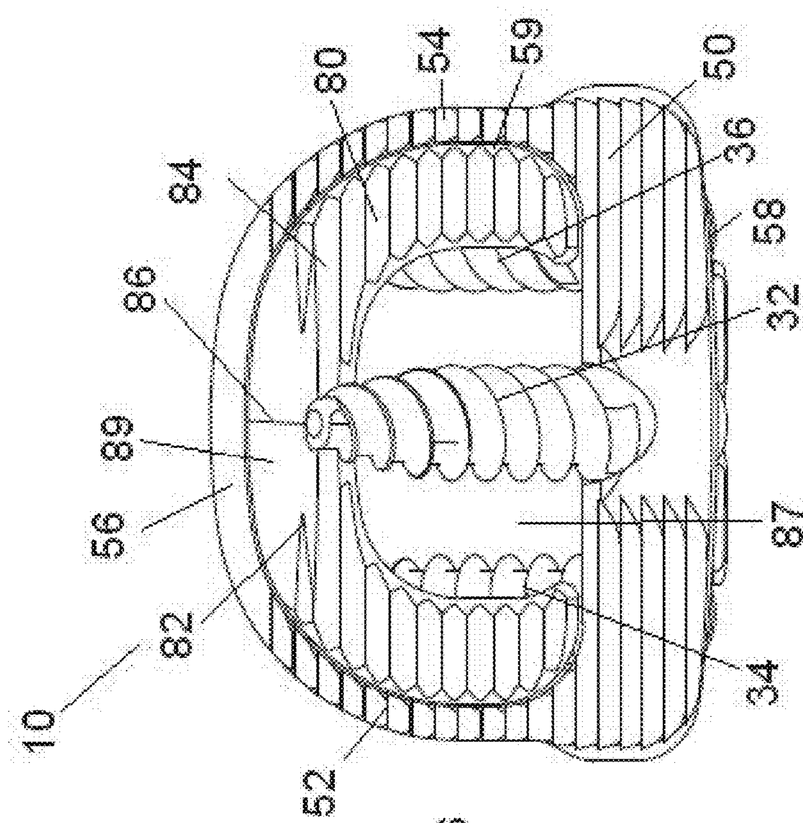
FIG. 3 shows a top view of the frame and spacer system of FIG. 1.

In some embodiments, the spacer 80 can comprise a multi-piece spacer that can be formed of a first member 82 joined to a second member 84 (as shown in FIG. 3). Each of the members 82, 84 can include a protruding portion 84 that can be received in a corresponding window of the frame 50. The first member 82 and the second member 84 can be joined together via an adhesive, pins, or other attachment means, thereby forming the C-shaped member. In the C-shaped spacer, the first member 82 forms a first arm of the C-shaped spacer while the second member 84 forms a second arm of the C-shaped spacer. By providing a multi-piece spacer, the spacer 80 is capable of having a large footprint, which is particularly useful for patients having large anatomies and disc spaces. In some embodiments, the spacer 80 can be formed of more than two members, such as three, four, five or more members that are attached to one another to form a unitary spacer 80.

Figure 2:
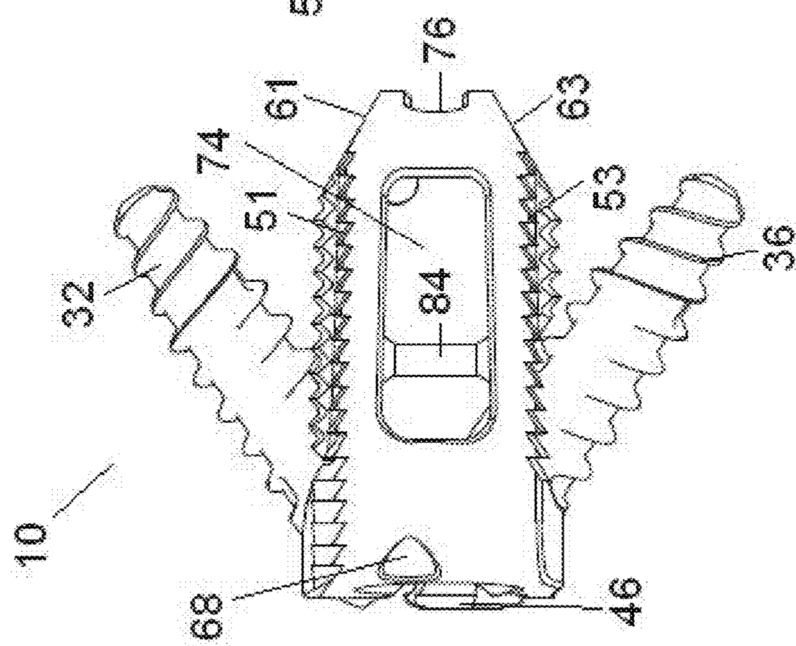
FIG. 2 shows a side view of the frame and spacer system of FIG. 1.

FIG. 2 shows a side view of the frame and spacer system of FIG. 1. From this view, one can see the shape of the frame 50 in accordance with some embodiments. The frame 50 includes an upper chamfer 61 and a lower chamfer 63 that forms a tapered leading end. Advantageously, the upper chamfer 61 and the lower chamfer 63 can aid in distraction and/or insertion of the frame 50 into a disc space. In addition, from this view, the upper surface of the frame 50 appears substantially parallel to the lower surface of the frame 50. However, in some embodiments, one or both of the upper surface and/or lower surface can be curved (e.g., convex). From this view, one can also see the second window 74 and the third window 76 that are formed through different surfaces of the frame 50. As shown in the figure, the spacer 80 includes a protruding portion 84 that is received in the second window 74, thereby securing the frame 50 to the spacer 80.

Figure 23:
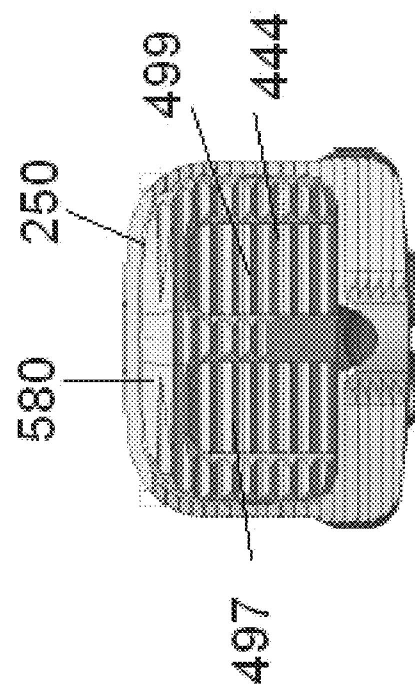
FIG. 23 is a top view of a frame and spacer system, wherein the spacer has a substantially flat side and includes a pair of graft chambers in accordance with some embodiments.
Figure 22:
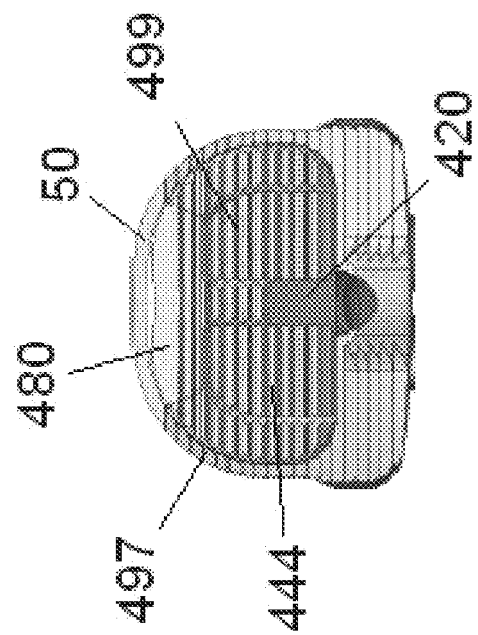
FIG. 22 is a top view of a frame and spacer system, wherein the spacer has a convex side and includes a pair of graft chambers in accordance with some embodiments.

FIG. 3 shows a top view of the frame and spacer system of FIG. 1. The spacer 80 is nested in the opening 59 of the frame 50. The spacer 80 is formed of a first member 82 and a second member 84 attached to one another at an interface 86 to form a C-shaped implant. The two members 82, 84 surround a spacer opening 87 through which a plug or graft material can be deposited therein. In some embodiments, a plug such as a cancellous plug (as shown in FIGS. 22 and 23) can be deposited in the spacer opening 87. As shown in FIG. 3, the spacer 80 can comprise of a convex leading end and a concave trailing end. The spacer 80 can comprise an upper chamfer 87 and a lower chamfer. In some embodiments, the upper chamfer and lower chamfer of the spacer 80 substantially match the upper and lower chamfer of the frame 50.

From this view, one can also see the overall shape of the frame 50. The first side 52 and second side 54 of the frame 50 can be curved. The third side 56, or leading side, of the frame 50 can also be curved. The fourth side 58, or trailing side, of the frame 50 can be flat or curved in accordance with some embodiments. As shown in FIG. 3, the fourth side 58, which houses the fixation members and blocking members, has a greater thickness than the third side 56.

Figure 5:
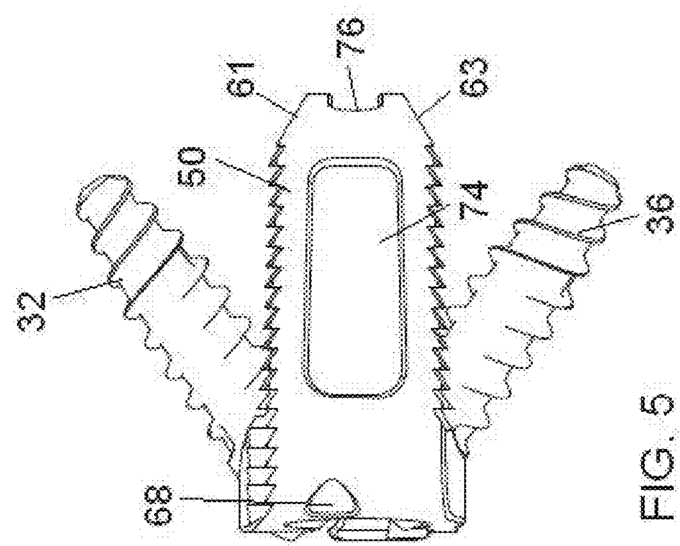
FIG. 5 is a side view of the frame of FIG. 4.
Figure 4:
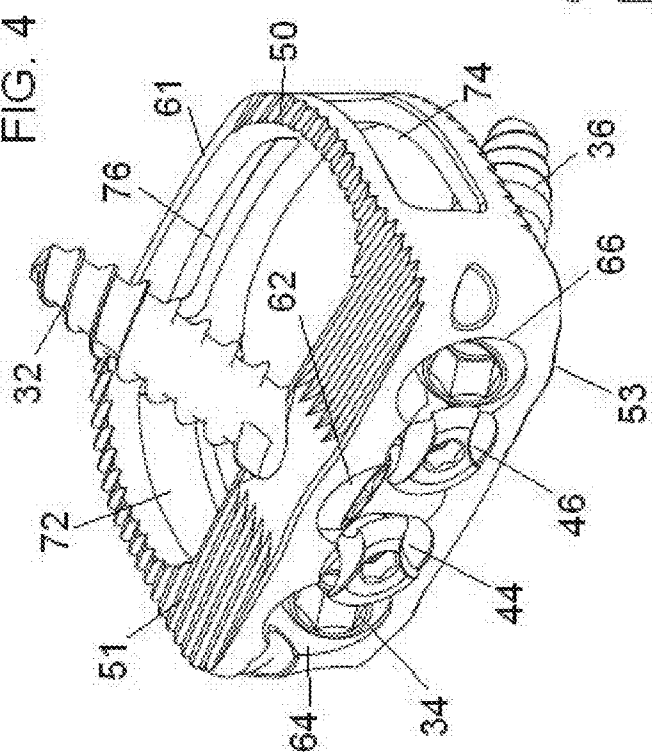
FIG. 4 shows a top perspective view of a frame with fixation members in accordance with some embodiments.

FIG. 4 shows a top perspective view of a frame with fixation members in accordance with some embodiments, while FIG. 5 is a side view of the same frame. The frame 50 can advantageously be used as a standalone device that is operable on its own without a spacer 80. From this view, one can see how the frame 50 includes a first window 72, a second window 74 and a third window 76. One or more of the windows can permit graft material to extend therethrough, thereby promoting fusion in a disc space.

Figures 6, 7:
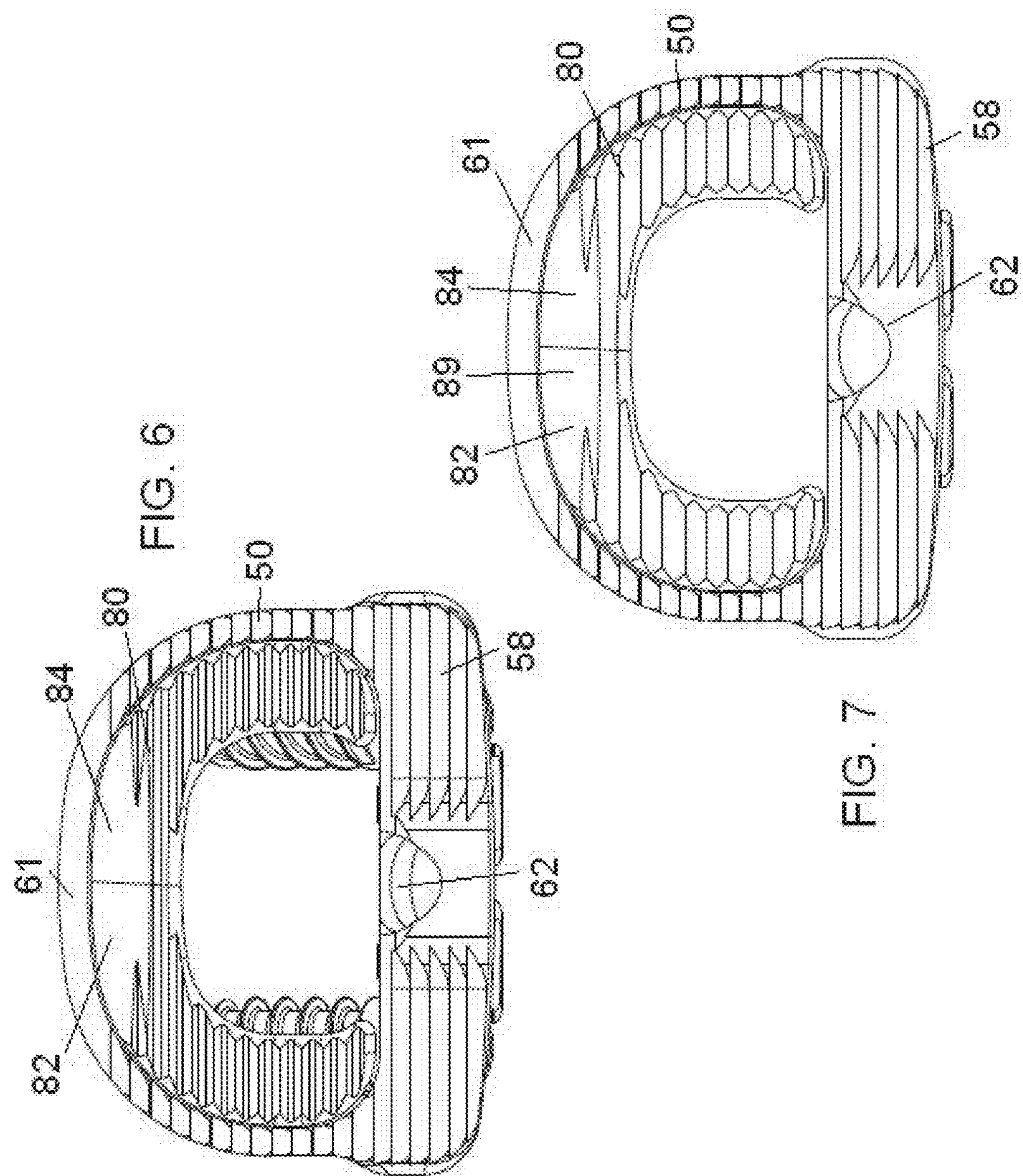
FIG. 6 is a top view of a frame and spacer system without an upper fixation member in accordance with some embodiments.
FIG. 7 is a top view of a frame and spacer system without fixation members in accordance with some embodiments.

FIG. 6 is a top view of a frame and spacer system without an upper fixation member in accordance with some embodiments. With the upper or first fixation member 32 removed, one can see how the first opening 62 extends through the fourth side 58 of the frame 50. As shown in FIG. 6, the first opening 62 begins and extends through an anterior surface of the fourth side 58 of the frame 50, and exits through an edge of a posterior surface of the fourth side 58 of the frame 50.

FIG. 7 is a top view of a frame and spacer system without fixation members in accordance with some embodiments. With the upper or first fixation member 32 removed, one can see how the first opening 62 extends through the fourth side 58 of the frame 50. As shown in FIG. 7, the first opening 62 begins and extends through an anterior surface of the fourth side 58 of the frame 50, and exits through an edge of a posterior surface of the fourth side 58 of the frame 50.

Figures 8, 9:
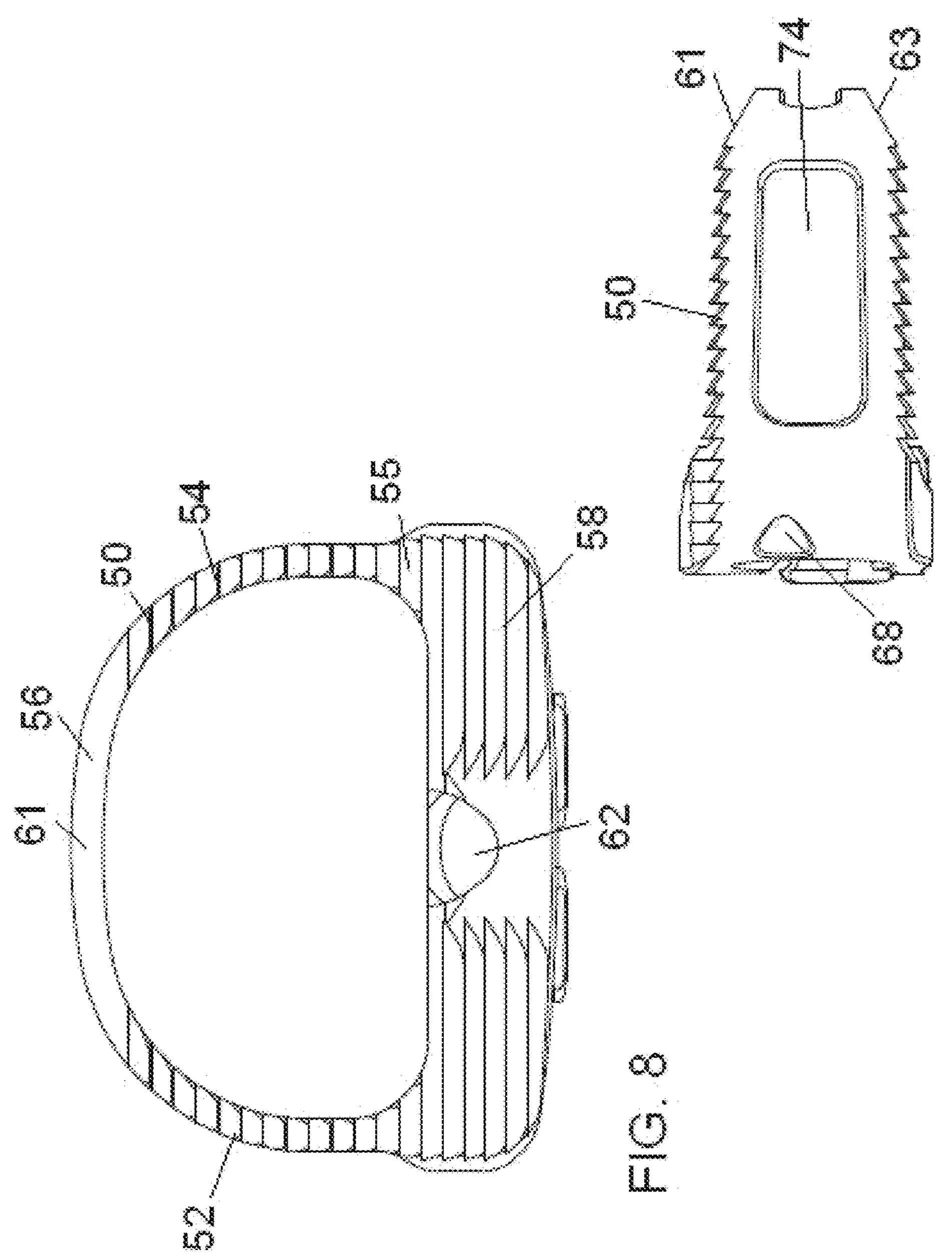
FIG. 8 is a top view of a frame in accordance with some embodiments.
FIG. 9 is a side view of the frame of FIG. 8.

FIG. 8 is a top view of a frame, while FIG. 9 is a side view of the frame, in accordance with some embodiments. The frame 50 is shown without a spacer 80 or any of the fixation elements. The frame 50 includes a convex anterior or leading end, as well as a slightly convex posterior or trailing end. The anterior end has an upper chamfer 61 and a lower chamfer 63 (shown in FIG. 2). The frame 50 includes a number of surface protrusions, teeth, ribbing or ridges 55 that provide engagement surfaces with adjacent vertebrae. As shown in FIG. 8, portions of the upper and/or lower chamfered surfaces of the spacer 80 do not include ridges 55.

Figure 10:
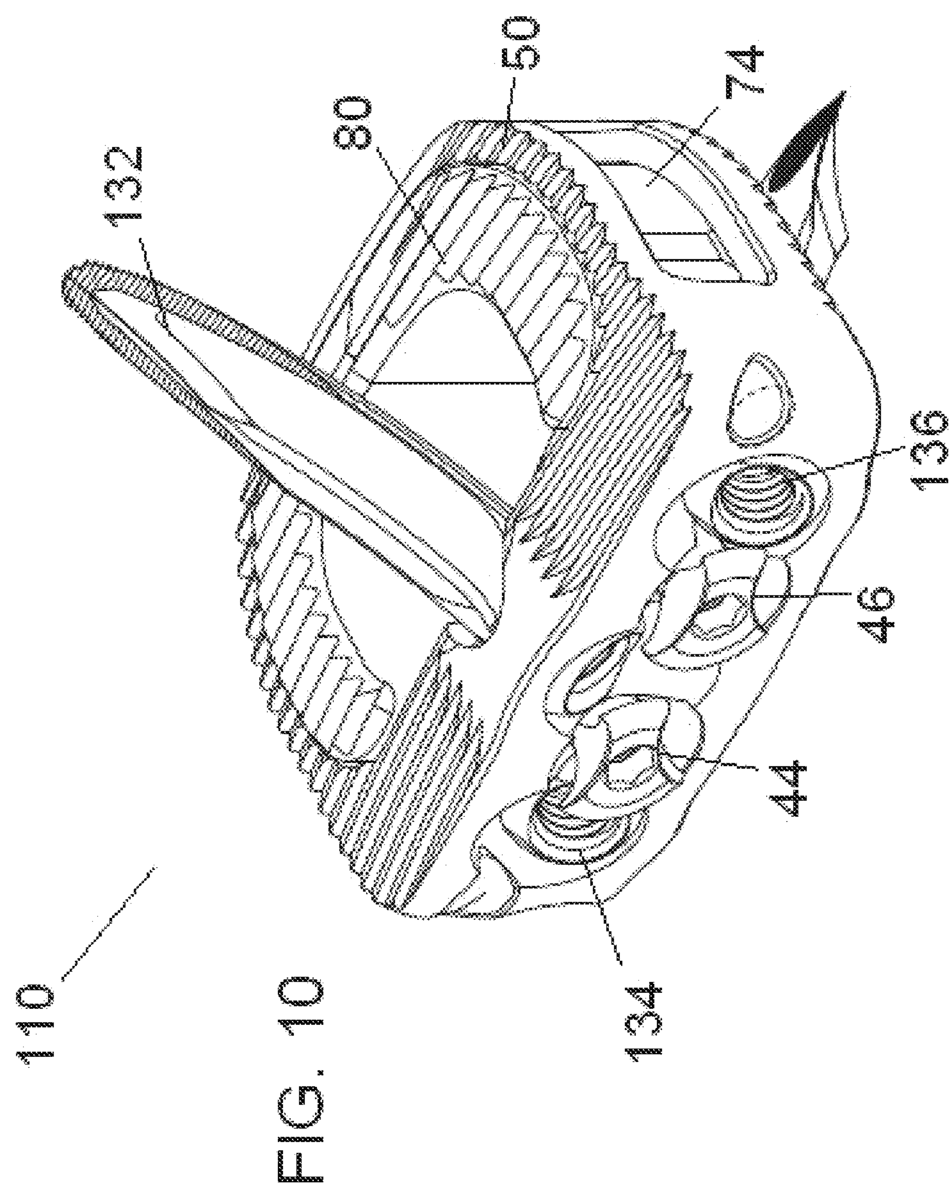
FIG. 10 is a top perspective view of a frame and spacer system having alternative fixation members in accordance with some embodiments.

FIG. 10 is a top perspective view of a frame and spacer system having alternative fixation members in accordance with some embodiments. The frame and spacer system 110 shares many similar features as in prior embodiments, including a frame 50 for receiving fixation members and a spacer 80 received therein. A first fixation member 132, a second fixation member 134, and a third fixation member 136 are received through the frame 50. However, in the present embodiment, each of the fixation members 132, 134, 136 are blades or shims. Advantageously, the fixation members 132, 134, 136 can be non-threaded such that they are easily inserted into bone, thereby saving time.

Figure 11:
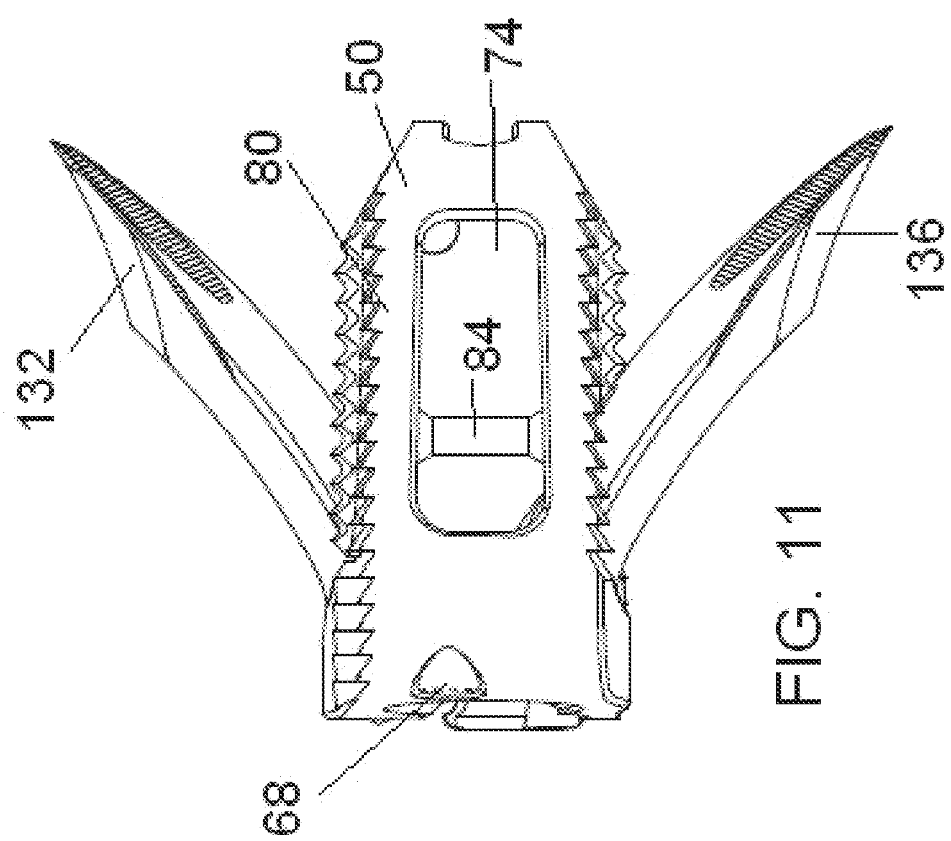
FIG. 11 is a side view of the frame and spacer system of FIG. 10.

FIG. 11 is a side view of the frame and spacer system of FIG. 10. From this view, one can see the first fixation member 132 and the third fixation member 136, which are non-threaded. In addition, one can see how the spacer 80 is retained in the frame 80 via one or more bump outs or protruding portions 84.

Figure 13:
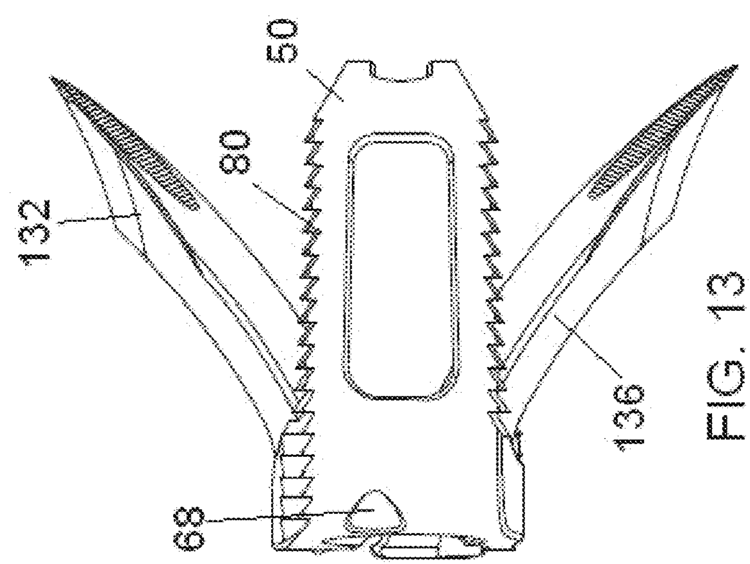
FIG. 13 is a side view of the frame of FIG. 12.
Figure 12:
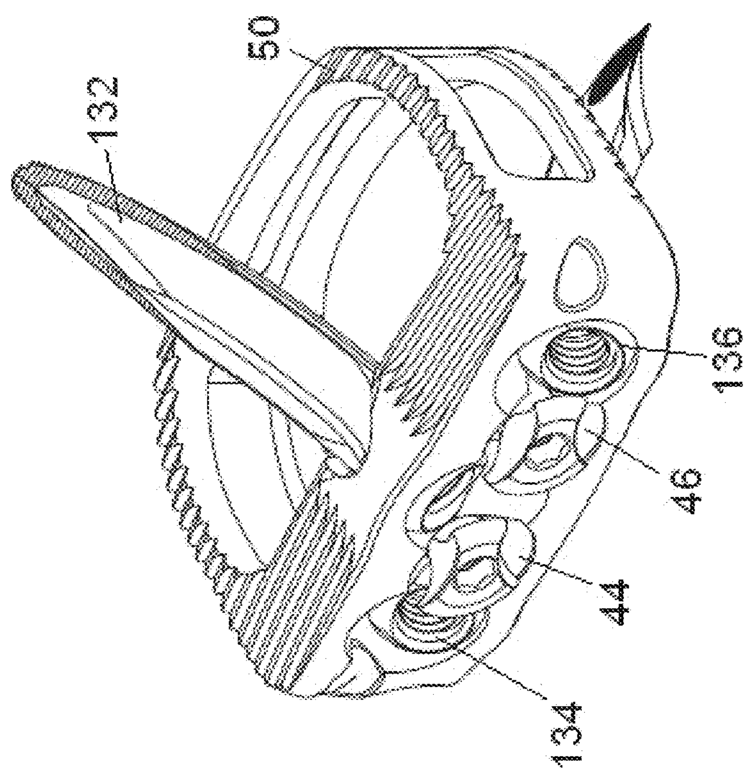
FIG. 12 is a top perspective view of a frame with alternative fixation members in accordance with some embodiments.

FIG. 12 is a top perspective view of a frame with alternative fixation members in accordance with some embodiments, while FIG. 13 is a side view. The frame 50 can be a standalone frame that can be used on its own without a spacer. In some embodiments, the frame 50 has a height that enables it to support a load, and is configured to receive one or more fixation members 132, 134, 136 to secure the frame 50 to vertebral bodies.

Figure 14:
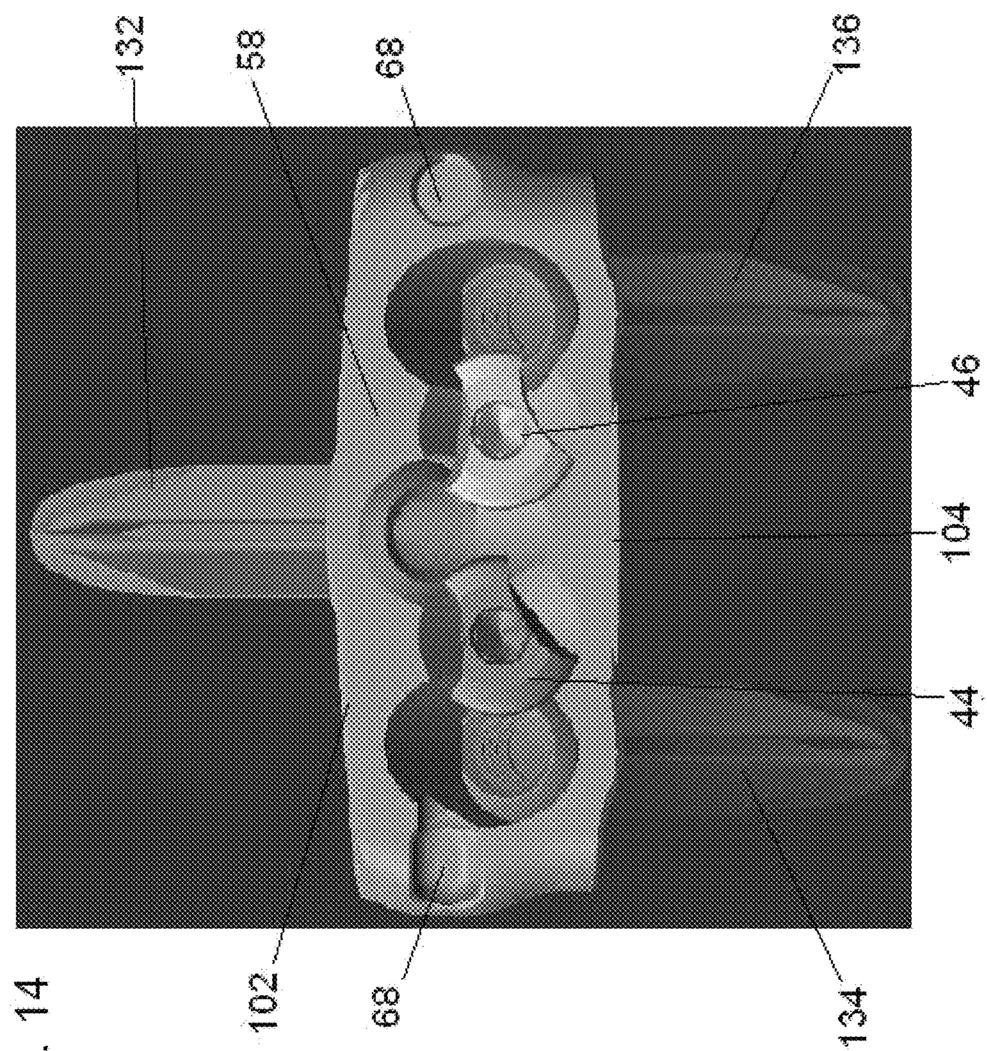
FIG. 14 is an anterior view of the frame of FIG. 12.

FIG. 14 is an anterior view of the frame of FIG. 12. As shown in the figure, the frame 50 includes an upper surface 102 and a lower surface 104. In some embodiments, the upper surface 102 is convex. In some embodiments, the lower surface 104 is convex. From this view, one can also see how the first blocking member 44 and the second blocking member 46 cover the upper heads of the fixation members 132, 134, 136 to reduce the likelihood of backout of the fixation members. Each of the blocking members 44, 46 resides in a recess that is formed adjacent a pair of openings. Each of the blocking members 44, 46 thus serves as a multi-block device, capable of reducing the risk of backout of two fixation members.

Figure 15:
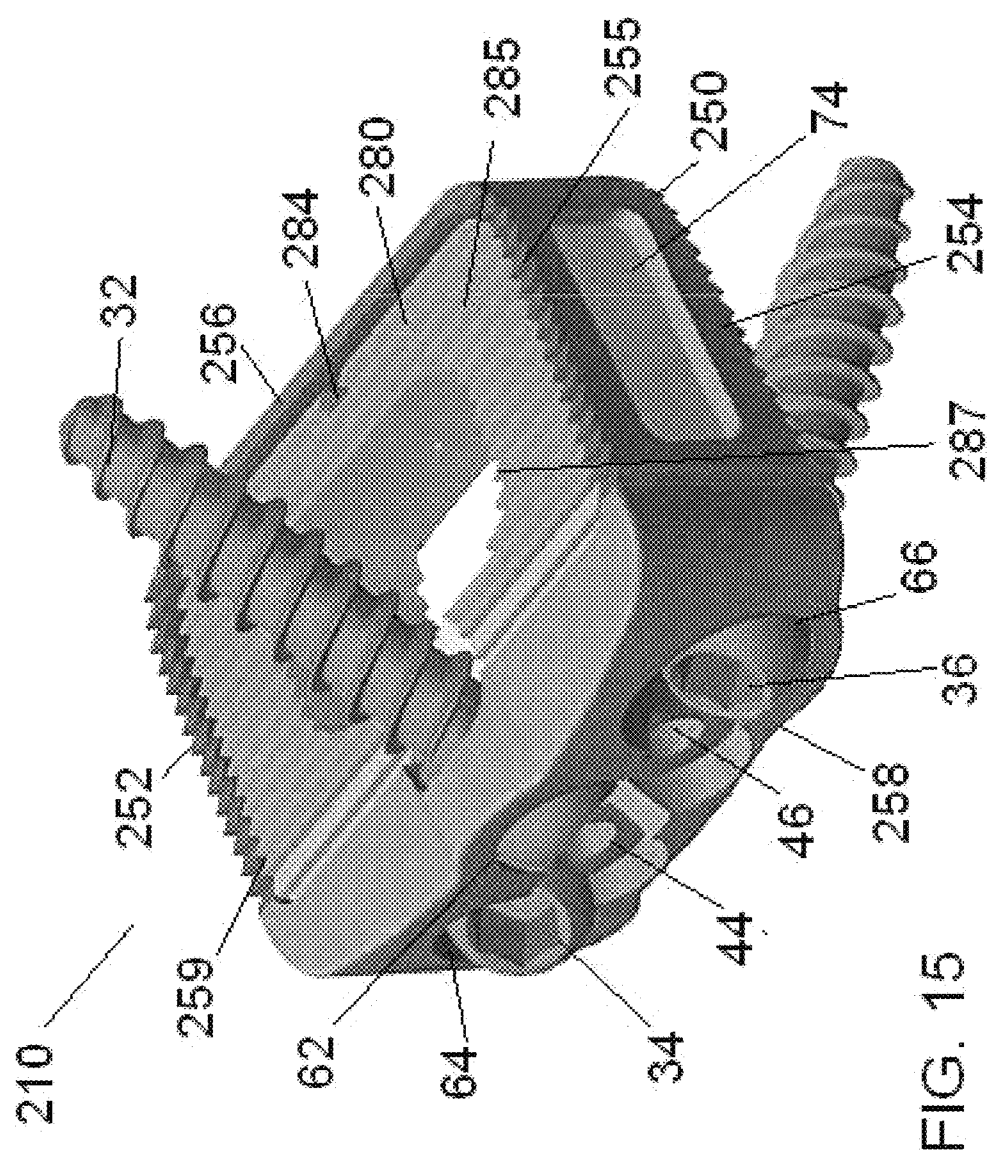
FIG. 15 is a top perspective view of a rectangular frame and spacer system in accordance with some embodiments.

FIG. 15 is a top perspective view of a rectangular frame and spacer system in accordance with some embodiments. The system 210 includes a rectangular cage or frame 250 that receives a spacer 280 therein.

The frame 250 comprises a first side 252, a second side 254, a third side 256, and a fourth side 258. The sides 252, 254, 256, 258 form a continuous perimeter for receiving a spacer 280 therein. First side 252 opposes the second side 254, while third side 256 opposes the fourth side 258. In some embodiments, the third side 256 can be considered a posterior or leading end, while the fourth side 258 can be considered an anterior or trailing end. As shown in FIG. 15, the fourth side 258 includes a first opening 62 for receiving a first fixation member 32, a second opening 64 for receiving a second fixation member 34 and a third opening 66 for receiving a third fixation member 36. In the present embodiment, the fixation members 32, 34, 36 are all threaded screws, while in other embodiments, one or more of the fixation members can be non-threaded blades or shims.

As in prior embodiments, frame includes one or more windows 74 which can serve one or more functions. In some embodiments, the windows 72, 74 (shown in FIG. 20) can be used to receive graft material therethrough. In addition, the windows 72, 74 can be used to retain one or more bump out or protruding portions of the spacer 280, thereby helping to secure the spacer 280 with the frame 250.

Additionally, in some embodiments, the frame 250 includes one or more protrusions or nubs 294 (shown in FIG. 20) that can also be used to secure the frame 250 to the spacer 280. As shown in FIG. 15, the spacer 280 can include one or more grooves or notches 284 formed along a sidewall that can receive the one or more nubs 294 therein. Advantageously, in some embodiments, the combination of the one or more nubs 294 and the one or more notches 284 forms a tight friction or interference fit, thereby securing the frame 250 to the spacer 280. In the present embodiment, the frame 250 includes a single nub 294 formed along an inner wall of its third side 256. However, in other embodiment, the frame 250 can include one, two, three or more nubs 294 formed on different inner walls.

The spacer 280 is configured to be received within an opening 259 in the frame 250. As in prior embodiments, the spacer 280 can be formed of PEEK or allograft, as desired by the surgeon. The spacer 280 is configured to include an opening 287 therein. In some embodiments, graft material is received in the opening 287. In other embodiments, a plug can be received in the opening 287. The spacer 280 can be formed of one, two, three, four or more members that are assembled 0 together via an adhesive or mechanical connection assembly. In the present embodiment, the spacer 280 has an overall rectangular profile that is configured to substantially match the contour of the frame 250.

As shown in FIG. 15, the spacer 280 includes one or more grooves or notches 284 for receiving one or more nubs 294 of the frame 250. The one or more notches 284 advantageously help to secure the frame 250 to the spacer 280. The notches 284 can be formed vertically along an outer wall of the spacer 280. For example, in the embodiment in FIG. 15, the notch 284 is formed on an outer wall of the spacer 280 that is adjacent the leading or third side of the frame 250. In other embodiments, the frame 250 can include one or more notches, while the spacer 280 includes one or more nubs, thereby creating a friction fit between the two members.

Figure 16:
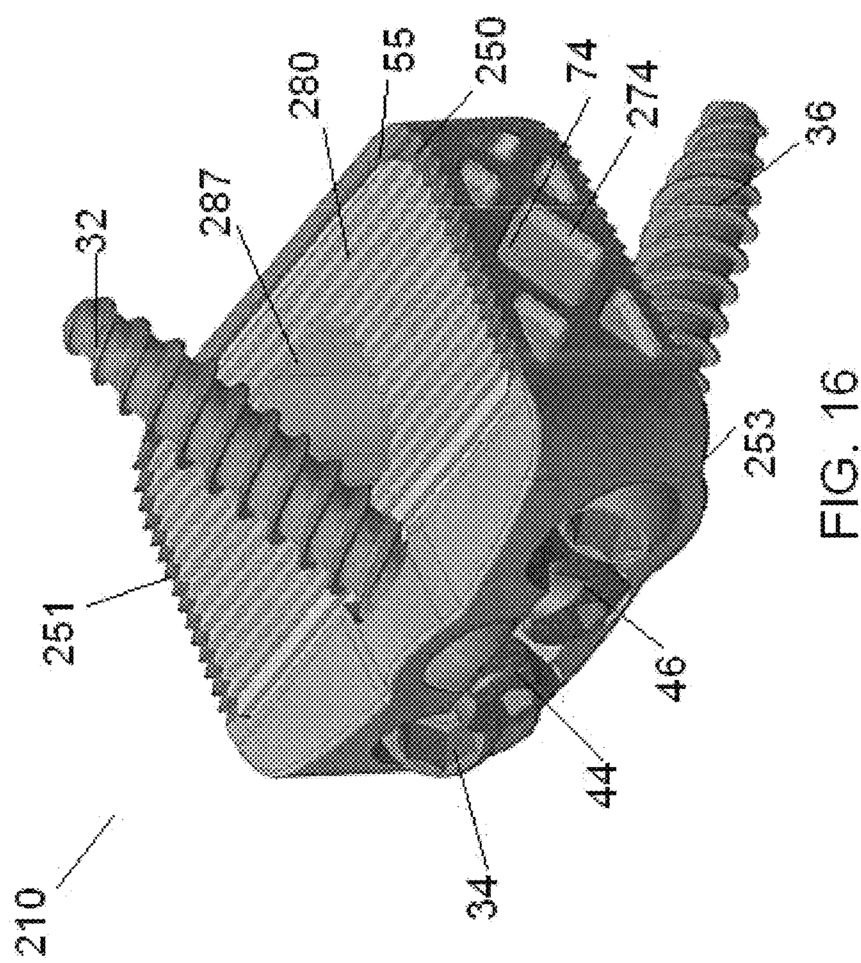
FIG. 16 is a top perspective view of an alternative rectangular frame and spacer system in accordance with some embodiments.

FIG. 16 is a top perspective view of an alternative rectangular frame and spacer system in accordance with some embodiments. The frame and spacer system 210 has many similar features to that shown in FIG. 15, including a top surface 251 and a bottom surface 253, and four walls that provide a continuous perimeter around a spacer. However, in the present embodiment, the frame 250 includes at least one side including multiple windows 74 in the form of a lattice 274. By providing the windows in the form of a lattice 274, this advantageously provides multiple sites of possible bone growth along the side of the frame 250.

Figure 18:
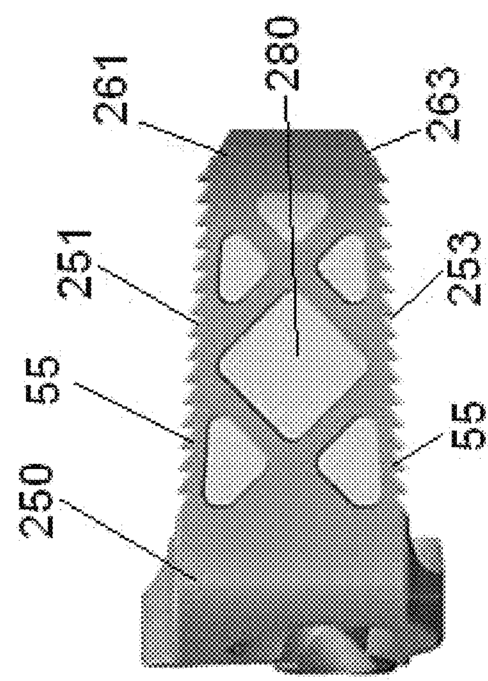
FIG. 18 is a side view of a rectangular frame and spacer system without fixation members in accordance with some embodiments.
Figure 17:
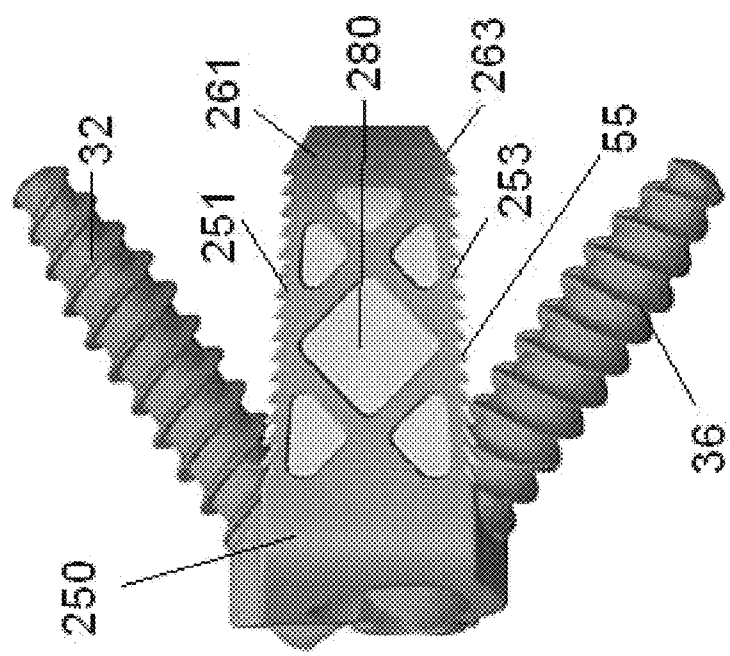
FIG. 17 is a side view of a rectangular frame and spacer system in accordance with some embodiments.

FIG. 17 is a side view of a rectangular frame and spacer system in accordance with some embodiments, while FIG. 18 is a side view of a rectangular frame and spacer system without fixation members in accordance with some embodiments. From these views, one can see how the spacer 280 is received in the frame 250. As shown in the figures, the spacer 280 can have a height that is the same as or less than the height of the frame 250. Also, from these views, one can see how the frame 250 includes ridges 55 that protrude upwardly from its surface to assist in engagement with bone. The frame 250 includes an upper chamfer 261 and a lower chamfer 263.

Figure 20:
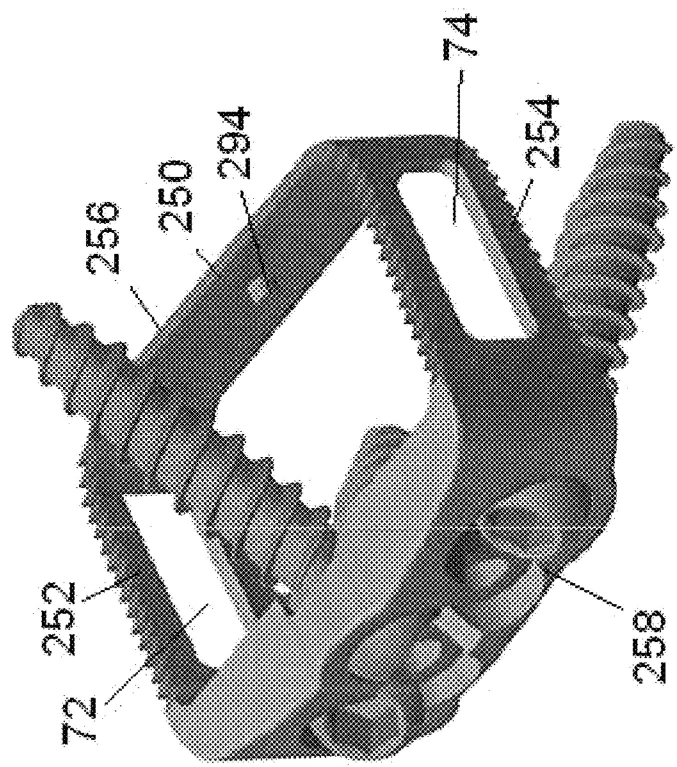
FIG. 20 is a top perspective view of an alternative rectangular frame in accordance with some embodiments.
Figure 19:
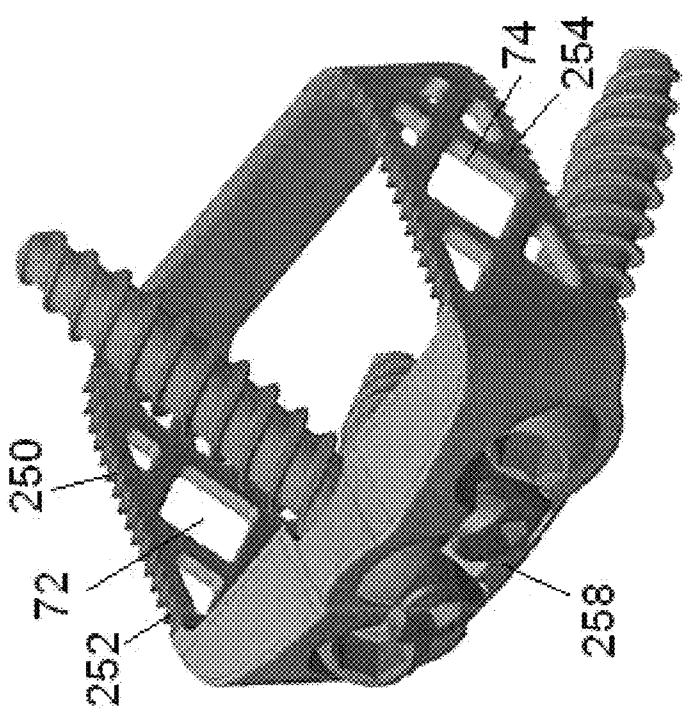
FIG. 19 is a top perspective view of a rectangular frame in accordance with some embodiments.

FIG. 19 is a top perspective view of a rectangular frame in accordance with some embodiments, while FIG. 20 is a top perspective view of an alternative rectangular frame in accordance with some embodiments. As in prior embodiments, the frame 250 can be a standalone frame wherein it can be inserted into a disc space without including a spacer if desired.

Figure 21:
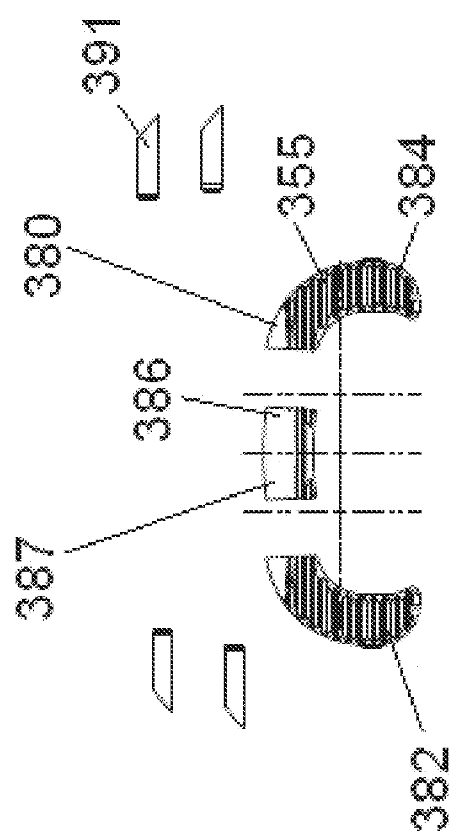
FIG. 21 is an exploded view of a spacer in accordance with some embodiments.

FIG. 21 is an exploded view of a spacer in accordance with some embodiments. As shown in FIG. 21, the spacer 380 can be a multi-piece spacer formed of different members that are connected together via one or more connection mechanisms (e.g., pins). The spacer 380 can be formed of any suitable biocompatible material, including metal, PEEK or bone. In particular, spacers 380 that are formed of bone (e.g., allograft) may benefit from being formed of multiple members, as this allows spacers are greater sizes to be formed. The spacer 380 includes an upper surface and a lower surface including surface texturing, protrusions, teeth or ridges 355 formed thereon.

In FIG. 21, the spacer 380 includes a first member 382, a second member 384 and a third member 386. When the members 382, 384, 386 are joined together, they form a C-shaped spacer 380, similar to that shown in FIG. 1. In some embodiments, each of the members 382, 384, 386 includes a chamfered upper surface and a chamfered lower surface, such that when the members are joined, the spacer 380 includes an upper chamfer and a lower chamfer. For example, as shown in FIG. 21, the spacer 380 will include an upper chamfer 387.

As shown in FIG. 21, the different members 382, 384, 386 of the spacer 380 can be secured together via one or more pin members 391. In some embodiments, the one or more pin members 391 can be formed of a similar material as one or more members 382, 384, 386 of the spacer 380. In some embodiments, one or more members 382, 384, 386 of the spacer 380 can be formed of allograft bone, and one or more pin members 391 can also be formed of allograft bone. In some embodiments, the one or more pin members 391 are formed at an angle other than parallel or 90 degrees relative to an interface formed between two members. In addition, in some embodiments, the one or more pin members 391 are received in blind pin holes, whereby at least one side of the pin holes is not exposed or open. In other embodiments, the one or more pin members 391 are received in non-blind pin holes. While in FIG. 21, the different members 382, 384, 386 are positioned horizontally to one another, in other embodiments, the different members can be stacked and connected vertically to one another.

FIG. 22 is a top view of a frame and spacer system, wherein the spacer has a convex side and includes a pair of graft chambers in accordance with some embodiments. In the present embodiment, the system comprises a frame 50 and a spacer 480 that is received within the frame 50. Advantageously, the spacer 480 is in the form of an E-shape, such that it has a first chamber 497 and a second chamber 499. The chambers 497, 499 are separated by a strut 420 formed on the frame 50. Advantageously, both the first chamber 497 and the second chamber 499 are capable of receiving a plug 444 therein, as shown in FIG. 22. In some embodiments, one or more of the plugs 444 is formed of bone (e.g., cortical or cancellous) and assists in fusion. In some embodiments, one or more of the plugs 444 includes bone fibers. In some embodiments, one or more of the plugs 444 is demineralized. By providing a pair of chambers 497, 499 for receiving bone-growth material therein, this advantageously increases the area for promoting bone-growth material. In addition, it allows for multiple smaller pieces of bone growth material (e.g., two plugs) to be used, as opposed to fewer larger pieces of bone growth material, which can be difficult to source.

FIG. 23 is a top view of a frame and spacer system, wherein the spacer has a substantially flat side and includes a pair of graft chambers in accordance with some embodiments. The spacer 580 is similar to the spacer 480 in that it includes a first chamber 497 independent from a second chamber 499. The overall shape of the spacer 580, however, is more like a rectangle, such that it is designed to fit within a substantially rectangular region of a frame.

FIG. 24 is a top view of a spacer including a convex side and a pair of graft chambers in accordance with some embodiments. The spacer 480 is an E-shaped spacer having a first chamber 497 and a second chamber 499. The spacer 480 includes a convex outer wall 495. In the present embodiment, the spacer 480 is formed of four members: a first member 482, a second member 484, a third member 486 and a fourth member 488.

FIG. 25 is an anterior view of the spacer of FIG. 24. From this view, one can see how the spacer 480 includes a convex upper surface 481 and a convex lower surface 483. Accordingly, the spacer 480 can advantageously have convexity in multiple planes, thereby accommodating different anatomical features. In some embodiments, the spacer 480 has convexity in at least two planes: an X-Y plane (as shown in FIG. 24) and an X-Z plane (as shown in FIG. 25). The spacer 480 can be considered biconvex in two planes.

FIG. 26 is a side view of the spacer of FIG. 24. From this view, one can see how the spacer 480 includes an upper surface 481, an opposing lower surface 483, an upper chamfer 489 and a lower chamfer 491. In some embodiments, the spacer can be in the form of a wedge member that is able to self-distract between two vertebrae in preparation for performing a fusion procedure.

FIG. 27 is a top view of a spacer including a substantially flat side and a pair of graft chambers in accordance with some embodiments. The spacer 580 is an E-shaped spacer having a first chamber 597 and a second chamber 599. The spacer 580 includes a slightly curved outer wall 595. In the present embodiment, the spacer 580 is formed of three members: a first member 582, a second member 584, and a third member 586.

FIG. 28 is an anterior view of the spacer of FIG. 27. From this view, one can see how the spacer 580 includes a convex upper surface 581 and a convex lower surface 583. Accordingly, the spacer 580 can advantageously have convexity in multiple planes, thereby accommodating different anatomical features. In some embodiments, the spacer 580 has curvature in at least two planes: an X-Y plane (as shown in FIG. 27) and an X-Z plane (as shown in FIG. 28).

FIG. 29 is a side view of the spacer of FIG. 27. From this view, one can see how the spacer 580 includes an upper surface 581, an opposing lower surface 583, an upper chamfer 589 and a lower chamfer 591. In some embodiments, the spacer can be in the form of a wedge member that is able to self-distract between two vertebrae in preparation for performing a fusion procedure.

Methods of using the systems and devices are now provided. In some embodiments, a disc space is formed between a first vertebra and a second vertebra. A frame and spacer system 10, such as shown in FIG. 1, can be prepared to be delivered to the disc space. A surgeon can choose the type of spacer 80 to attach to the frame 50, and can then attach the elements together via a press mechanism. The spacer 80 can be retained in the frame 50 via bump out or protruding portions 84. The frame and spacer system 10 (without fixation members) can be attached to an insertion tool via its first and second tool engagement holes 68. The frame and spacer system 10 can then be delivered via the tool into the disc space, such as via an anterior approach. The frame and spacer system 10 is of a low profile such that it is positioned completely within the disc space. Optional graft material could be packed within the frame and spacer system 10 prior to delivery. Once the frame and spacer system 10 is positioned within the disc space, one or more fixation members 32, 34, 36 can be delivered to secure the frame 50 and spacer 80 to the first and second vertebrae. The frame and spacer system 10 can be left in the surgical site, whereby it will be used to promote fusion and bone growth.

In alternative embodiments, a standalone frame 50, as shown in FIG. 4, can be prepared to be delivered to the disc space. The standalone frame 50 can be delivered to the disc space without a spacer 80. The frame 50 (without fixation members) can be attached to an insertion tool via its first and second tool engagement holes 68. The frame 50 can then be delivered via the tool into the disc space, such as via an anterior approach. The frame 50 is of a low profile such that it is positioned completely within the disc space. Optional graft material could be packed within the frame 50 prior to delivery. Once the frame 50 is positioned within the disc space, one or more fixation members 32, 34, 36 can be delivered to secure the frame 50 to the first and second vertebrae. The standalone frame 50 can be left in the surgical site, whereby it will be used to promote fusion and bone growth.

FIG. 30 is a top perspective view of an alternative frame and spacer system in accordance with some embodiments. The frame and spacer system 610 includes similar features as in prior embodiments, including a frame 650, a spacer 680, a first fixation member 632, a second fixation member 634 and a third fixation member 636. The frame 650 comprises an upper surface 651 and a lower surface 653, each of which is designed to engage a vertebral member. The frame 650 includes an opening 659 for receiving the spacer 680 therein. Moreover, the frame 650 includes openings for receiving fixation members 632, 634, 636 therein. To prevent back out of the fixation members 632, 634, 636, a first blocking member 644 and a second blocking member 646 can be provided. In addition to these features, the frame and spacer system 610 has distinct geometrical features that advantageously allow it to be of low profile and to better accommodate a patient's anatomy.

FIG. 31 is a front view of the alternative frame and spacer system of FIG. 30. From this view, one can see a front or anterior view of the frame 650. The frame 650 includes a distinct upper surface 660 that is advantageously designed to be low profile. In particular, the upper surface 660 comprises an arched portion 664 positioned between two adjacent slanted portions 662*a*, 662*b*. The slanted portions 662*a*, 662*b* have a height that is reduced relative to the arched portion 664, thereby enhancing the low profile of the frame 650. In some embodiments, the frame 650 can also include a lower surface of a similar shape to the upper surface 660 to thereby reduce the overall profile of the frame and spacer system 610.

FIG. 32 is a side view of the alternative frame and spacer system of FIG. 30. From the side view, one can see the first fixation member 632 that is angled upwardly and the third fixation member 636 which is angled downwardly.

Figure 34:
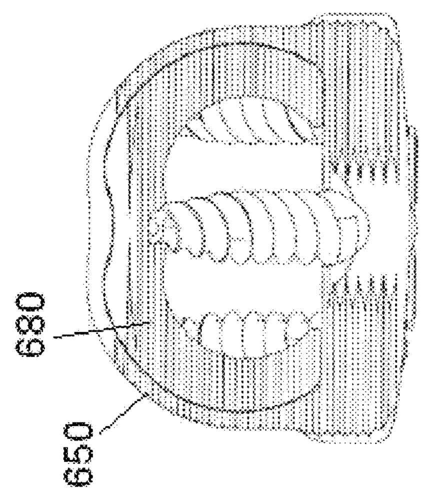
FIG. 34 is a top view of the alternative frame and spacer system of FIG. 30 with fixation members.
Figure 33:
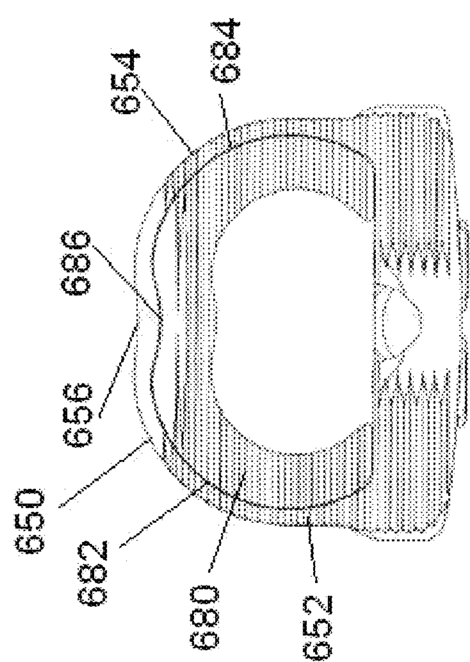
FIG. 33 is a top view of the alternative frame and spacer system of FIG. 30 without fixation members.

FIG. 33 is a top view of the alternative frame and spacer system of FIG. 30 without fixation members, while FIG. 34 is a top view of the alternative frame and spacer system with fixation members. As shown in the figure, the frame 650 comprises a first side 652, a second side 654, a third side 656 and a fourth side 658. The frame 650 advantageously encompasses a spacer 680 having a first side 682, a second side 684 and a third side 686. As shown in FIG. 33, in some embodiments, the frame 650 and the spacer 680 include a distinct shape and form that provides a better anatomical fit with certain patients. With respect to the frame 650, the first side 652 and the second side 654 comprise convexly curved surfaces, while the third side 656 comprises a concave surface. The spacer 680, which follows the contour of the frame 650, also has a first side 682 and second side 684 that comprise convexly curved surfaces and a third side 686 that comprises a concavely curved surface.

Figures 35, 36:
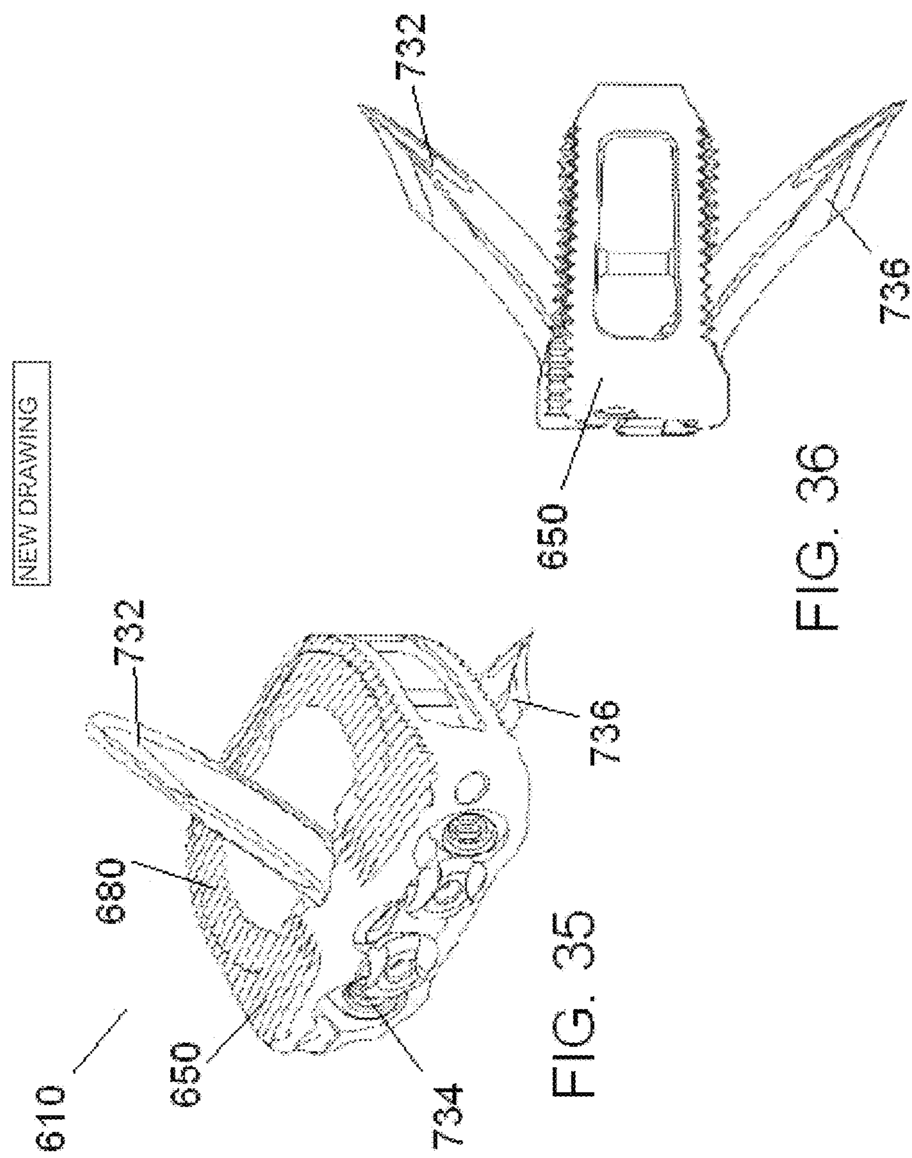
FIG. 35 is a top perspective view of the alternative frame and spacer system of FIG. 30 with alternative fixation members.
FIG. 36 is a side view of the alternative frame and spacer system of FIG. 30 with alternative fixation members.

FIG. 35 is a top perspective view of the alternative frame and spacer system of FIG. 30 with alternative fixation members, while FIG. 36 is a side view of the same system. The frame and spacer system 610 comprises a frame 650 and a spacer 680 with non-threaded blades or shims 732, 734, 736 received through the frame 650.

Figure 37:
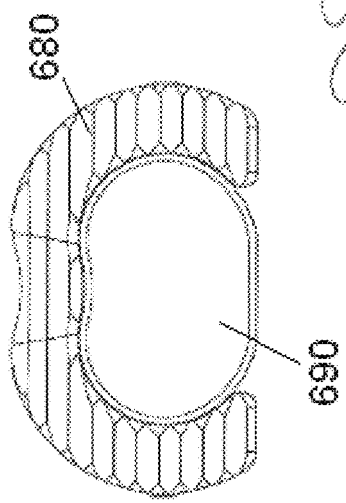
FIG. 37 is a top view of a spacer and plug in accordance with some embodiments.
Figure 38:
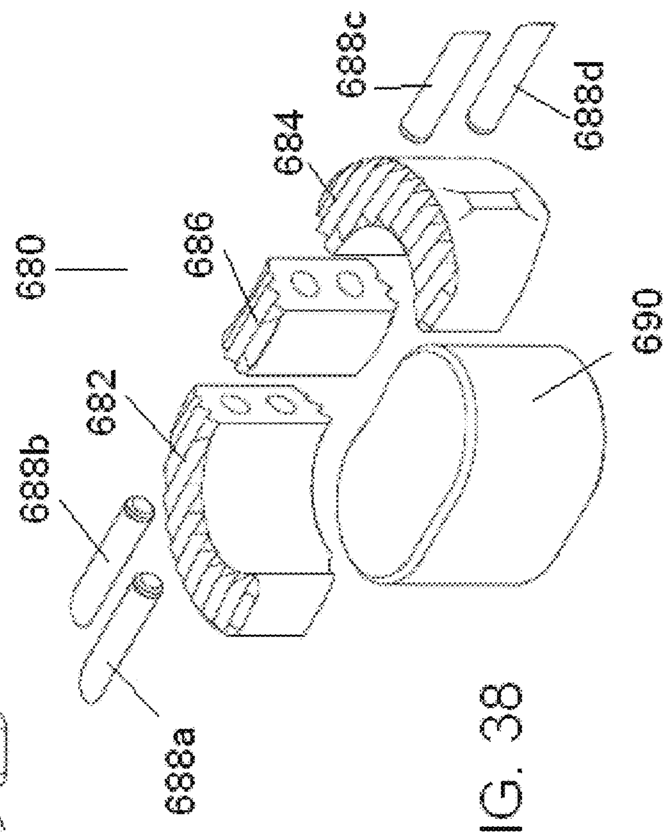
FIG. 38 is an exploded view of the spacer and plug of FIG. 37.

FIG. 37 is a top view of a spacer and plug in accordance with some embodiments. The spacer 680 and plug 690 can advantageously be used with any of the frames (such as frame 650) shown above. In some embodiments, the spacer 680 is formed of PEEK or allograft. In the present embodiment, the spacer 680 is formed of allograft bone and is formed of multiple members assembled together (as shown in FIG. 38). In some embodiments, the plug 690 is formed of a natural material, such as bone (e.g., cancellous bone). The advantage of providing such a plug 690 is that it helps to promote enhanced fusion.

FIG. 38 is an exploded view of the spacer and plug of FIG. 37. As shown in the figure, the spacer 680 is formed of a first member 682, a second member 684 and a third member 686 held together via pins 688*a*, 688*b*, 688*c*, 688*d*. In some embodiments, the pins 688*a*, 688*b*, 688*c*, 688*d* are also formed of bone. A first pair of pins 688*a*, 688*b* is received through the interface between the members 682, 686, while a second pair of pins 688*c*, 688*d* is received through the interface between the members 684, 686.

The systems described above can be used with a number of different surgical implants. Among the surgical implants include stabilization implants, including plates, screws (e.g., pedicle screws) and rods. In addition, more than one frame and spacer system can be applied, such as to different levels of the spine. In addition, the frame and spacer systems described above can be used with different prosthetic devices, such as facet devices.

It will be apparent to those skilled in the art that various modifications and variations can be made in the present invention without departing from the scope or spirit of the invention. Moreover, the frame and spacer systems described above need not feature all of the objects, advantages, features and aspects discussed above. Thus, for example, those skilled in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed bone screw assemblies. Thus, it is intended that the present invention cover the modifications and variations of this invention provided that they come within the scope of the appended claims or their equivalents.

What is claimed is:

1. A surgical system comprising:

a frame, wherein the frame comprises a first side, a second side, a third side, and a fourth side that form a continuous perimeter around a frame opening, and wherein the frame includes an upper surface extending between the first side, the second side, the third side, and the fourth side, a portion of the upper surface comprising an arched surface disposed in between a first slanted portion and a second slanted portion;

a spacer received in the frame opening, wherein the spacer comprises a first portion defining a first side surface and terminating at a first distal end, a second portion defining a second side surface and terminating at a second distal end, wherein a gap is defined between the first and second distal ends, and a third portion connecting the first and second portions, the third portion defining a third side surface, wherein the first side surface and the second side surface each comprise a convex surface, wherein the third side surface comprises a concave surface corresponding engaged with the perimeter of the frame opening; and one or more fixation members insertable in the frame, wherein the one or more fixation members includes at least a first fixation member that is angled in an upward direction and a second fixation member that is angled in a downward direction wherein the first distal end and the second distal end are free ends.

2. The surgical system of claim 1, wherein the frame comprises a first window and a second window.

3. The surgical system of claim 2, wherein the spacer comprises a first protruding portion and a second protruding portion, wherein the first protruding portion is configured to be received in the first window and the second protruding portion is configured to be received in the second window.

4. The surgical system of claim 1, wherein the frame comprises an upper chamfer and a lower chamfer.

5. The surgical system of claim 1, wherein the frame includes a first opening, a second opening and a third opening, wherein the first opening is configured to receive the first fixation member, the second opening is configured to receive the second fixation member, and the third opening is configured to receive a third fixation member.

6. The surgical system of claim 1, wherein the spacer is formed of allograft bone.

7. The surgical system of claim 1, wherein the spacer is formed of multiple members secured to one another via pin members.

8. The surgical system of claim 7, wherein the spacer is formed of a first member, a second member and a third member that connected to each other horizontally.

9. The surgical system of claim 1, wherein the spacer is configured to receive a cancellous plug therein.

10. The surgical system of claim 1, wherein the spacer is C-shaped.

11. A surgical system comprising:

a frame, wherein the frame comprises a leading end, a trailing end, a first sidewall, and a second sidewall that form a continuous perimeter around a frame opening, and wherein the frame includes an upper surface extending between the leading end, the trailing end, the first sidewall, and the second sidewall, a portion of the upper surface comprising an arched surface disposed in between a first slanted portion and a second slanted portion;

a spacer received in the frame opening, wherein the spacer comprises a first portion defining a first side surface and terminating at a first distal end, a second portion defining a second side surface and terminating at a second distal end, wherein a gap is defined between the first and second distal ends, and a third portion connecting the first and second portions, the third portion defining a third side surface, wherein the first side surface and the second side surface each comprise a convex surface, wherein the third side surface comprises a concave surface corresponding engaged with the perimeter of the frame opening; and one or more fixation members insertable in the trailing end of the frame, wherein the one or more fixation members includes at least a first fixation member that is angled in an upward direction and a second fixation member that is angled in a downward direction wherein the first distal end and the second distal end are free ends.

12. The surgical system of claim 11, wherein the leading end is convex.

13. The surgical system of claim 11, wherein the first sidewall comprises a first window and the second sidewall comprises a second window.

14. The surgical system of claim 13, wherein at least one of the first window and the second window is in the form of a lattice.

15. The surgical system of claim 11, wherein the spacer is biconvex in two planes.

16. The surgical system of claim 11, wherein the spacer is formed of at least a first member joined to a second member via a pin.

17. The surgical system of claim 16, wherein the first member, second member and pin are all comprised of the same material.

18. The surgical system of claim 11, wherein the leading end includes a first tool engagement hole and a second tool engagement hole.

19. The surgical system of claim 11, wherein the frame comprises a first opening for receiving the first fixation member which is non-threaded, a second opening for receiving the second fixation member which is non-threaded, and a third opening for receiving a third non-threaded fixation member.

20. The surgical system of claim 11, wherein the frame has a generally similar height to the spacer.

* * * * *